US011242571B2

(12) United States Patent
Gao et al.

(10) Patent No.: US 11,242,571 B2
(45) Date of Patent: Feb. 8, 2022

(54) METHOD TO HOMOGENIZE PARVOVIRUS B19 IN CLINICAL SAMPLES

(71) Applicant: Grifols Diagnostic Solutions Inc., Emeryville, CA (US)

(72) Inventors: Kui Gao, San Diego, CA (US); Jeffrey M. Linnen, Poway, CA (US)

(73) Assignee: GRIFOLS DIAGNOSTIC SOLUTIONS INC., Emeryville, CA (US)

( * ) Notice: Subject to any disclaimer, the term of this patent is extended or adjusted under 35 U.S.C. 154(b) by 0 days.

(21) Appl. No.: 16/348,046

(22) PCT Filed: Jan. 25, 2019

(86) PCT No.: PCT/IB2019/050618
§ 371 (c)(1),
(2) Date: May 7, 2019

(87) PCT Pub. No.: WO2019/145900
PCT Pub. Date: Aug. 1, 2019

(65) Prior Publication Data

US 2021/0115523 A1 Apr. 22, 2021

Related U.S. Application Data

(60) Provisional application No. 62/623,113, filed on Jan. 29, 2018.

(51) Int. Cl.
*C12Q 1/70* (2006.01)
*C12N 7/00* (2006.01)

(52) U.S. Cl.
CPC ............... *C12Q 1/701* (2013.01); *C12N 7/00* (2013.01); *C12N 2750/14321* (2013.01)

(58) Field of Classification Search
None
See application file for complete search history.

(56) References Cited

U.S. PATENT DOCUMENTS

| | | | | |
|---|---|---|---|---|
| 6,946,254 | B2 | 9/2005 | Yang et al. | |
| 2011/0306038 | A1* | 12/2011 | Carrick | C12Q 1/701 435/5 |
| 2016/0201144 | A1* | 7/2016 | Chelliserry | C12Q 1/6893 435/6.11 |
| 2017/0022480 | A1* | 1/2017 | Buno | C12Q 1/706 |

FOREIGN PATENT DOCUMENTS

| | | | |
|---|---|---|---|
| EP | 3 121 268 | A1 | 1/2017 |
| JP | 2005505268 | A | 2/2005 |
| JP | 201723144 | A | 2/2017 |
| WO | 2010099378 | A2 | 9/2010 |
| WO | 2016064887 | A1 | 4/2016 |
| WO | 2016183282 | A1 | 11/2016 |

OTHER PUBLICATIONS

European Office Action for corresponding European Application No. 19 705 825.8 dated Apr. 30, 2020, 3 pages.
Japanese Office Action for corresponding Japanese Application No. 2019-520553 dated Jun. 22, 2020, 17 pages.
International Search Report pertaining to International Application No. PCT/IB2019/050618, filed Jan. 25, 2019, 11 pages.
Saldanha, J. et al., Detection of human parvovirus B19 DNA in plasma pools and blood products derived from these pools: implications for efficiency and consistency of removal of B19 DNA during manufacture. British Journal of Hematology, Jun. 1, 1996, p. 714-719, vol. 93, No. 3, Wiley-Blackwell Publishing Ltd., Great Britain.

* cited by examiner

*Primary Examiner* — Shanon A. Foley
(74) *Attorney, Agent, or Firm* — Dinsmore & Shohl LLP

(57) ABSTRACT

Various aspects of the invention relate to compositions and methods of analyzing blood plasma, blood serum, and manufacturing pools of plasma-derived products wherein an anionic surfactant is added to an aliquot of the blood plasma, blood serum, or manufacturing pool prior to analysis, and the counterion of the anionic surfactant is not sodium ion. The anionic surfactant may be, for example, lauryl sulfate. The counterion of the anionic surfactant may be, for example, lithium ion.

32 Claims, 9 Drawing Sheets

METHOD TO HOMOGENIZE PARVOVIRUS B19 IN CLINICAL SAMPLES

CROSS-REFERENCE TO RELATED APPLICATIONS

This application is a National Stage application of International Application PCT/IB2019/050618, filed Jan. 25, 2019, which claims priority to U.S. Provisional Application No. 62/623,113, filed Jan. 29, 2018, the entire contents of both of which are incorporated by reference herein in their entirety.

BACKGROUND

Various regulatory agencies including the European Medicines Agency and U.S. Food & Drug Administration require testing for a number of different viruses during the production of plasma-derived products and releasing blood components from normal blood donation including hepatitis A virus, hepatitis B virus, hepatitis C virus, human immunodeficiency virus 1 and 2, and parvovirus B19. Although parvovirus B19 infection typically does not cause chronic health problems, parvovirus B19 from high-titer plasma donations can cause severe adverse reactions in patients receiving plasma-derived products.

Plasma donations containing high titers of parvovirus B19 are frequent and can contaminate plasma pools. Contaminated plasma pools in turn allow parvovirus B19 to be transmitted by plasma-derived products including coagulation factors, fibrin sealants, and solvent/detergent treated plasma.

Parvovirus B19 titer is typically quantified by nucleic acid testing to exclude high titer donations from plasma pools, which can significantly reduce contamination and transmission. Parvovirus B19 is challenging to quantify in some plasma samples due to the aggregation of viral particles, however, and improved methods to quantify parvovirus B19 are desirable.

SUMMARY

Various aspects of the embodiments relate to a method of determining the concentration of human parvovirus B19 in human blood plasma or a manufacturing pool of a human plasma-derived product. A method may comprise contacting a sample with a surfactant solution comprising an anionic surfactant thereby producing a treated sample. The sample may comprise an aliquot of either human blood plasma or a manufacturing pool of a human plasma-derived product. The sample may consist of an aliquot of either human blood plasma or a manufacturing pool of a human plasma-derived product. The method may further comprise determining whether the concentration of human parvovirus B19 in the aliquot is above or below a threshold value. In preferred embodiments, the molar ratio of sodium to anionic surfactant in the surfactant solution is less than 1:10.

The anionic surfactant may be lauryl sulfate.

The surfactant solution may consist essentially of the anionic surfactant (e.g., lauryl sulfate), a counterion thereof (e.g., lithium), and water. The surfactant solution may consist of the anionic surfactant (e.g., lauryl sulfate), a counterion thereof (e.g., lithium), and water (i.e., and lack any other molecules or ions except for unavoidable contaminants).

In some embodiments, the contacting occurs at a temperature of about 4° C. to about 37° C.

In some embodiments, the molar ratio of lithium cation to anionic surfactant in the surfactant solution is about 1:2 to about 2:1 such as about 1:1.

In some embodiments, the concentration of the anionic surfactant in the treated sample is at least 4% (weight/volume) such as at least 5%, from 4% to 10% or from 5% to 10%.

In some embodiments, determining whether the concentration of human parvovirus B19 in the aliquot is above or below a threshold value comprises nucleic acid testing such as transcription mediated amplification (TMA) or polymerase chain reaction (PCR). In certain embodiments, the nucleic acid testing is capable of detecting all known genotypes of human parvovirus B19.

In certain embodiments, the method further comprises discarding the human blood plasma, the manufacturing pool, or a downstream manufacturing pool thereof if the concentration of human parvovirus B19 in the aliquot is greater than the threshold value.

In some embodiments, the method further comprises measuring the concentration of human parvovirus B19 in the sample thereby obtaining a measurement. In certain preferred embodiments, the coefficient of variation of different measurements obtained for different aliquots of the same human blood plasma or the same manufacturing pool is no more than 50% for aliquots that are contacted with the surfactant solution and that undergo the same sample preparation and analysis steps to determine whether the concentration of human parvovirus B19 in the different aliquots is above or below the threshold value; and the coefficient of variation of different measurements obtained for different aliquots of the same human blood plasma or the same manufacturing pool is greater than 50% for aliquots that are not contacted with the surfactant solution but that otherwise undergo the same sample preparation and analysis steps to determine whether the concentration of human parvovirus B19 in the different aliquots is above or below the threshold value.

Various aspects of the embodiments relate to a method of manufacturing a plasma-derived product, comprising determining a concentration of human parvovirus B19 in an aliquot of blood plasma or a manufacturing pool and the manufacturing a plasma-derived product from the human blood plasma or manufacturing pool if the concentration of human parvovirus B19 in the aliquot is less than a threshold value. The plasma-derived product may be, for example, pooled plasma, solvent/detergent treated pooled plasma, a coagulation factor, a fibrin sealant, albumin, or an immunoglobulin product.

Various aspects of the embodiments relate to a plasma-derived product manufactured according to the methods described herein.

Various aspects of the embodiments relate to a composition comprising a Parvoviridae virus genome; an anionic surfactant; and at least two amplification primers that each specifically bind either a nucleotide sequence of a Parvoviridae virus genome or a reverse complement thereof thereby allowing the amplification of a Parvoviridae virus nucleotide sequence. The composition may comprise a liquid. The liquid may comprise the Parvoviridae virus genome and the anionic surfactant. In preferred embodiments, the molar ratio of the anionic surfactant to any sodium ion present in the liquid is greater than 1:1.

In some embodiments, the at least two amplification primers allow for the amplification of a nucleotide sequence of each known genotype of human parvovirus B19.

In some embodiments, the composition further comprises a solid support, wherein the solid support is a bead, a membrane, a microtiter plate, a polypeptide chip, or the solid-phase of a chromatography column. The composition may further comprise an oligonucleotide that is immobilized on the solid support.

In some embodiments, the anionic surfactant comprises an aliphatic chain comprising 6 to 26 carbon atoms. For example, the aliphatic chain may be saturated and/or unbranched, e.g., and the anionic surfactant may lack an unbranched, linear carbon chain other than the aliphatic chain. In some embodiments, the anionic surfactant lacks any carbon atoms other than the carbon atoms of the aliphatic chain. In preferred embodiments, the anionic surfactant has a net charge of about −1 at pH 5 to 10. The anionic surfactant can be selected from an organosulfate, sulfonate, organophosphate, organophosphonate, or carboxylate. For example, in preferred embodiments, the anionic surfactant is lauryl sulfate.

In some embodiments, the concentration of the anionic surfactant in the liquid is at least 4% (weight/volume) such as 4% to about 10% (weight/volume), about 5% to about 10% (weight/volume), 4% to about 9% (weight/volume), or about 5% to about 9% (weight/volume).

In preferred embodiments, the concentration of sodium ion in the liquid is less than 1% (weight/volume). In some embodiments, the concentration of lithium ion in the liquid is at least 0.01% (weight/volume).

In some embodiments, the Parvoviridae virus genome is of parvovirus B19.

In some embodiments, the composition comprises human blood plasma or a manufacturing pool of a human plasma-derived product.

Various aspects of the embodiments relate to a composition as described herein, wherein the Parvoviridae virus genome is of parvovirus B19; the anionic surfactant is lauryl sulfate; the concentration of lauryl sulfate in the liquid is at least 4% (weight/volume); the concentration of lithium ion in the liquid is at least 0.1% (weight/volume); the lithium and lauryl sulfate are present in the liquid at a molar ratio of about 11:10 to about 10:11; the concentration of sodium ion in the liquid is less than 0.5% (weight/volume); an aliquot of either human blood plasma or a manufacturing pool of a human plasma-derived product is dispersed within the composition; and the Parvoviridae virus genome of the composition is from the aliquot of the human blood plasma or the aliquot of the manufacturing pool.

DETAILED DESCRIPTION

Figure 1:
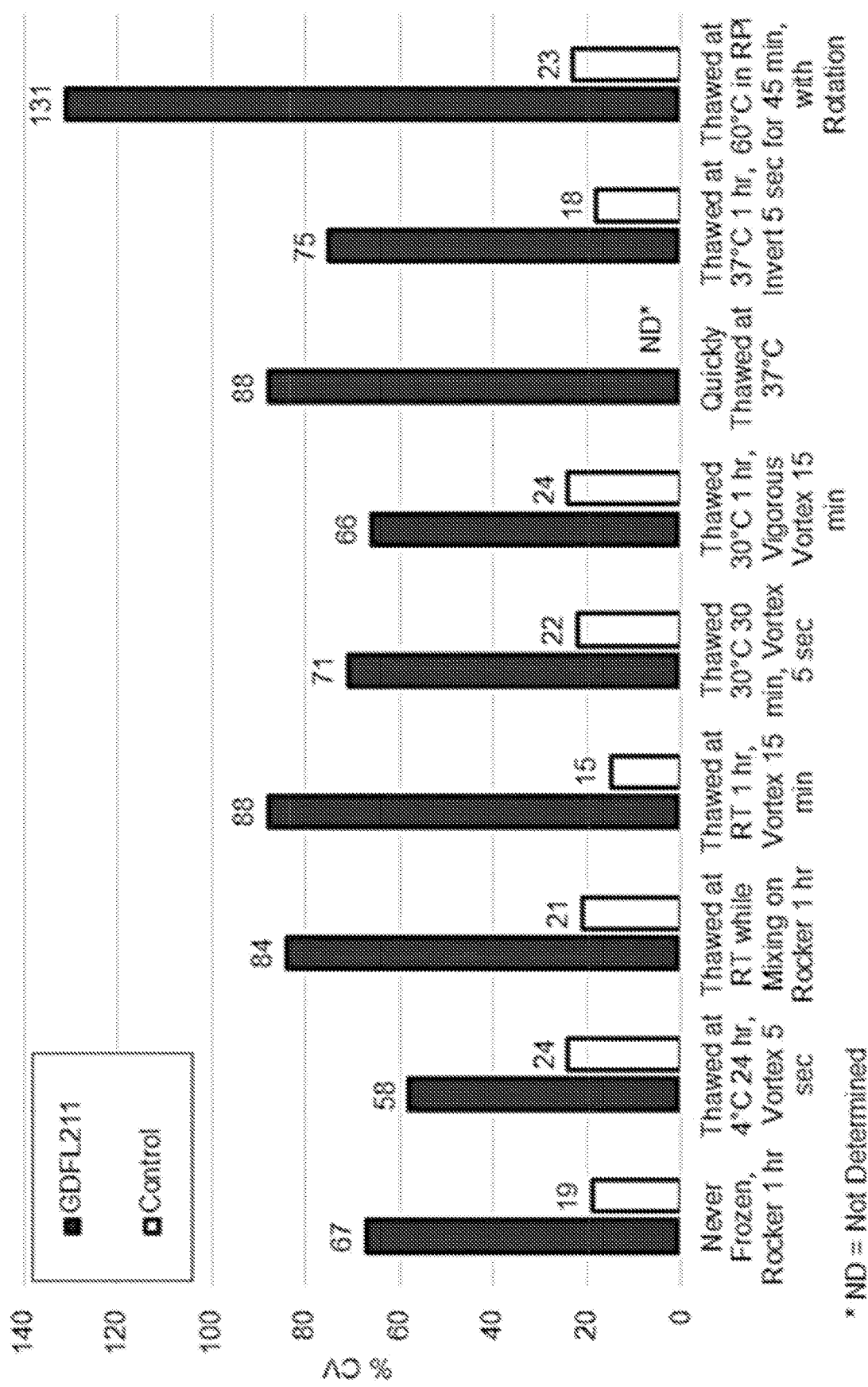
FIG. 1 is a bar graph displaying an analysis of the coefficient of variation (% CV) for aliquots from the challenging plasma sample GDFL211 (black bars) and a control plasma sample (white bars) that were analyzed by nucleic acid testing for parvovirus B19 after freezing and thawing under a variety of different conditions. The freeze/thaw/mixing conditions that were analyzed did not improve the coefficient of variation among different aliquots of plasma sample GDFL211 that underwent the same freeze/thaw protocol.

Various embodiments relate to the finding that the addition of lithium lauryl sulfate (LLS) to plasma allows for the detection of parvovirus B19 in the plasma with significantly increased precision. This is unexpected in that the commonly-used surfactant, sodium dodecyl sulfate (SDS), created precipitates in aliquots from the same plasma sample, and the analysis of SDS-treated plasma samples produced invalid results.

LLS and SDS include the same anionic surfactant lauryl sulfate, which is also known as dodecyl sulfate and laurisulfate. Lauryl sulfate is an organosulfate containing a single, unbranched, unsaturated, 12-carbon aliphatic group. LLS and SDS differ in that SDS includes the counterion sodium whereas LLS includes the counterion lithium, which suggests that sodium ion is at least partially responsible for the inability to analyze SDS-treated plasma samples. The selection of counterion thus plays an unexpected, but significant, role in methods such as are disclosed herein.

The commonly-used nonionic surfactant Triton X-100, which lacks a counterion, did not increase the precision of parvovirus B19 measurements in plasma samples. Accordingly, anionic surfactants were found to be necessary to improve the precision of parvovirus B19 measurement in plasma samples.

As described in detail in the Exemplification section, infra, the addition of LLS to various samples increased the precision of parvovirus B19 measurement under a variety of different conditions without affecting measurement accuracy. LLS is therefore a promising reagent for use in the screening of plasma, serum, and the manufacturing pools of plasma-derived products for elevated titers of parvovirus B19. LLS did not affect the sensitivity of the detection of hepatitis A virus (HAV) RNA in a WHO International Standard for HAV RNA, and thus, LLS may be generally applicable as a reagent for increasing the precision of measurements obtained from the analysis of blood, plasma, and serum samples.

A. Anionic Surfactants

Various aspects of the invention relate to an anionic surfactant. An anionic surfactant comprises a hydrophobic group and a net negative charge by definition. The nature of the hydrophobic group is not particularly limiting. The hydrophobic group can be, for example, an aliphatic chain. In some embodiments, the anionic surfactant comprises an aliphatic chain.

The nature of an aliphatic chain is not particularly limiting. The aliphatic chain can optionally include one or more double bonds, one or more triple bonds, one or more heteroatoms such as O, N, S, or Si, branching, one or more homocycles or heterocycles, and/or one or more substituents as are commonly-known. One or more protons of an aliphatic chain can optionally be substituted with a halogen such as F, Cl, Br, or I, a hydroxyl, or a thiol. The aliphatic chain can optionally include an ether, thioether, ester, or thioester.

An aliphatic chain can include, for example, 4 to 30 carbon atoms, such as 6 to 26, 8 to 20, or 10 to 16 carbon atoms. An aliphatic chain can include, e.g., at least 4, 5, 6, 7, 8, 9, 10, 11, 12, 13, 14, 15, 16, 17, 18, 19, 20, 21, 22, 23, 24, 25, or 26 carbon atoms. An aliphatic chain can include, e.g., 4, 5, 6, 7, 8, 9, 10, 11, 12, 13, 14, 15, 16, 17, 18, 19, 20, 21, 22, 23, 24, 25, or 26 carbon atoms.

In some embodiments, an anionic surfactant contains one aliphatic chain. In some embodiments, the anionic surfactant lacks any carbon atoms other than the carbon atoms of the aliphatic chain.

In some embodiments, the anionic surfactant does not occur in nature. For example, the anionic surfactant might not exist in either human blood or human blood plasma. In some embodiments, the anionic surfactant does not exist in human blood plasma. An anionic surfactant may nevertheless occur in nature; however, the anionic surfactant is typically not found in unadulterated human blood plasma, for example, at a concentration greater than 0.1% (weight/volume).

Common classes of anionic surfactants include sulfates, sulfonates, phosphates, phosphonates, and carboxylates, which identify the group form which a negative charge of the anionic surfactant may originate (e.g., a sulfate, sulfonate, phosphate, phosphonate, or carboxyl group).

Representative anionic surfactants that may be useful in various embodiments described herein include alkyl sulfates (e.g., lauryl sulfate), alkyl ether sulfates (e.g., laureth sulfate, myreth sulfate), dioctyl sulfosuccinate, lactylates (e.g., stearoyl lactylate), alkylbenzenesulfonates (e.g., dodecylbenzenesulfonate), perfluoro alkyl sulfonates (e.g., perfluorooctanesulfonate), alkyl phosphates, dialkyl phosphates, alkyl ether phosphates, alkyl-aryl ether phosphates, and fatty acids (e.g., stearate).

An aliphatic chain may be saturated or unsaturated, and the saturation or unsaturation of an aliphatic chain is not particularly limiting. Lauryl sulfate, for example, includes a saturated aliphatic chain. An aliphatic chain may be branched or unbranched, and the branching of an aliphatic chain is not particularly limiting. Lauryl sulfate, for example, includes an unbranched aliphatic chain. An aliphatic chain may be linear or cyclic, and this feature is not particularly limiting. Lauryl sulfate, for example, includes a linear aliphatic chain.

An anionic surfactant typically has a negative net charge at neutral pH, which is pH=7.4 as defined herein. A negative net charge as defined herein refers to a charge less than −0.5, which indicates that more than half of the molecules of an anionic surfactant have a negative charge under a given set of conditions (which is typically controlled by pH).

An anionic surfactant can have a net charge less than −0.5 at a pH of 1 to 14, such as pH 5 to 10, pH 5 to 7, pH 6 to 8, pH 7 to 9, or pH 8 to 10. An anionic surfactant can have a net charge of about −1 at a pH of 1 to 14, such as pH 5 to 10, pH 5 to 7, pH 6 to 8, pH 7 to 9, or pH 8 to 10.

The concentration of an anionic surfactant in a liquid composition depends upon the nature of the anionic surfactant and the concentration of other components of the liquid composition. For liquid compositions that comprise >10% human blood plasma such as >20%, >30%, >40%, >50%, >60%, >70%, >80%, or >90% human blood plasma, an anionic surfactant can be present, for example, at a concentration of at least about 1% such as at least about 2%, 3%, 4%, 5%, 6%, 7%, 8%, 9%, or 10% anionic surfactant.

An anionic surfactant may be present in a liquid composition at a concentration of about 1% to about 20% (weight/volume) such as about 3% to about 9%, about 4% to about 9%, about 1% to about 5%, about 3% to about 7%, about 5% to about 9%, about 1%, about 2%, about 3%, about 4%, about 5%, about 6%, about 7%, about 8%, about 9%, or about 10%.

An anionic surfactant may be present in a liquid composition at a concentration of about 100 mmol/L to about 1 mol/L such as about 150 mmol/L to about 500 mmol/L, about 150 mmol/L to about 350 mmol/L, about 100 mmol/L to about 200 mmol/L, about 150 mmol/L to about 250 mmol/L, about 200 mmol/L to about 300 mmol/L, about 250 mmol/L to about 350 mmol/L, about 120 mmol/L, about 130 mmol/L, about 140 mmol/L, about 150 mmol/L, about 160 mmol/L, about 170 mmol/L, about 180 mmol/L, about 190 mmol/L, about 200 mmol/L, about 210 mmol/L, about 220 mmol/L, about 230 mmol/L, about 240 mmol/L, about 250 mmol/L, about 260 mmol/L, about 270 mmol/L, about 280 mmol/L, about 290 mmol/L, or about 300 mmol/L.

The concentration of an anionic surfactant in a liquid composition is preferentially sufficient to increase the precision of a measurement of Parvovirus titer in the liquid composition. For example, the anionic surfactant is typically present in a liquid composition at a concentration great enough to reduce the coefficient of variation for replicates of a parvovirus B19 titer measurement in the liquid composition to less than about 70% for challenging samples, such as less than about 60%, less than about 50%, less than about 40%, or even less than about 30%. About 4% LLS, for example, is a concentration of the anionic surfactant LLS that is great enough to reduce the coefficient of variation for replicates of a parvovirus B19 titer measurement in a liquid composition to less than about 70% for challenging samples. Similarly, about 5% LLS is a concentration of the anionic surfactant LLS that is great enough to reduce the coefficient of variation for replicates of a parvovirus B19 titer measurement in a liquid composition to less than about 30% for challenging samples.

The term "challenging sample" as defined herein refers to a sample that displays a coefficient of variation that is both greater than 50% and greater than double the coefficient of variation of a typical sample or average sample such as the control sample described in the Exemplification section, infra, when measuring an analyte in the sample such as parvovirus B19 using a method such as nucleic acid testing (e.g., PCR).

B. Counterions

An anionic surfactant is typically present in aqueous solution with one or more cationic counterions, which are cations other than protons and hydronium ions. The terms "cationic counterion" and "counterion" as the terms are used herein do not include sodium ion unless sodium ion is explicitly included. The one or more cationic counterions typically comprise or consist of one or more hard Lewis acids, especially lithium ion, although the one or more cationic counterions can also include potassium ion, titanium ion, magnesium ion, calcium ion, aluminum ion, silicon ion, ammonium, lysine, histidine, or arginine.

C. Surfactant Solutions

A surfactant solution is typically a liquid comprising an anionic surfactant, a cationic counterion, and water. A surfactant solution may consist essentially of an anionic surfactant, a cationic counterion, and water. The anionic surfactant can be, for example, lauryl sulfate, which can be present in the surfactant solution at a concentration of at least about 10% (weight/volume) such as at least about 11%, 12%, 13%, 14%, 15%, 16%, 17%, 18%, 19%, or 20%. In some embodiments, the surfactant solution comprises lauryl sulfate at a concentration of about 10%, 11%, 12%, 13%, 14%, 15%, 16%, 17%, 18%, 19%, or 20%.

The surfactant solution may comprise the anionic surfactant at a concentration of at least about 175 mmol/L such as at least about 180 mmol/L, 190 mmol/L, 200 mmol/L, 225 mmol/L, 250 mmol/L, 275 mmol/L, 300 mmol/L, 325 mmol/L, 350 mmol/L, 375 mmol/L, 400 mmol/L, 450 mmol/L, 500 mmol/L, 550 mmol/L, 600 mmol/L, 650 mmol/L, 700 mmol/L, or 750 mmol/L.

The surfactant solution may comprise the anionic surfactant at a concentration of at least about 5% (weight/volume) such as at least about 5%, about 6%, about 7%, about 8%, about 9%, about 10%, about 11%, about 12%, about 13%, about 14%, about 15%, about 16%, about 17%, about 18%, about 19%, or about 20%.

The surfactant solution may comprise the anionic surfactant at a concentration of about 175 mmol/L to about 800 mmol/L, such about 200 mmol to about 800 mmol, about 400 mmol to about 800 mmol, about 600 mmol to about 800 mmol, about 300 mmol to about 500 mmol, about 400 mmol to about 600 mmol, about 500 mmol to about 700 mmol, about 600 mmol to about 800 mmol, about 700 mmol to about 800 mmol, about 180 mmol/L, about 190 mmol/L, about 200 mmol/L, about 225 mmol/L, about 250 mmol/L, about 275 mmol/L, about 300 mmol/L, about 325 mmol/L, about 350 mmol/L, about 375 mmol/L, about 400 mmol/L, about 450 mmol/L, about 500 mmol/L, about 550 mmol/L, about 600 mmol/L, about 650 mmol/L, about 700 mmol/L, or about 750 mmol/L.

The surfactant solution may comprise the anionic surfactant at a concentration of about 5% to about 30% such as about 10% to about 25%, about 10% to about 14%, about 12% to about 16%, about 14% to about 18%, about 16% to about 20%, about 18% to about 22%, about 20% to about 24%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25%.

In preferred embodiments, the surfactant solution is essentially free of sodium ion. Sodium ion may nevertheless be present in the surfactant solution, for example, at trace levels or at a molar ratio relative to the anionic surfactant that is substantially lower than 1:1 such as a sodium ion to anionic surfactant molar ratio of less than 1:5, 1:10, 1:20, 1:25, or 1:100. A surfactant solution may lack sodium ion.

The surfactant solution may comprise the cationic counterion at a concentration of at least about 175 mmol/L such as at least about 180 mmol/L, 190 mmol/L, 200 mmol/L, 225 mmol/L, 250 mmol/L, 275 mmol/L, 300 mmol/L, 325 mmol/L, 350 mmol/L, 375 mmol/L, 400 mmol/L, 450 mmol/L, 500 mmol/L, 550 mmol/L, 600 mmol/L, 650 mmol/L, 700 mmol/L, or 750 mmol/L.

The surfactant solution may comprise lithium ion at a concentration of at least about 175 mmol/L such as at least about 180 mmol/L, 190 mmol/L, 200 mmol/L, 225 mmol/L, 250 mmol/L, 275 mmol/L, 300 mmol/L, 325 mmol/L, 350 mmol/L, 375 mmol/L, 400 mmol/L, 450 mmol/L, 500 mmol/L, 550 mmol/L, 600 mmol/L, 650 mmol/L, 700 mmol/L, or 750 mmol/L.

The surfactant solution may comprise lithium ion at a concentration of at least about 0.001% (weight/volume) such as at least about 0.01%, about 0.05%, about 0.10%, about 0.11%, about 0.12%, about 0.13%, about 0.14%, about 0.15%, about 0.16%, about 0.17%, about 0.18%, about 0.19%, about 0.20%, about 0.21%, about 0.22%, about 0.23%, about 0.24%, about 0.25%, about 0.26%, about 0.27%, about 0.28%, about 0.29%, about 0.30%, about 0.31%, about 0.32%, about 0.33%, about 0.34%, about 0.35%, about 0.36%, about 0.37%, about 0.38%, about 0.39%, about 0.40%, about 0.41%, about 0.42%, about 0.43%, about 0.44%, about 0.45%, about 0.46%, about 0.47%, about 0.48%, about 0.49%, about 0.50%, about 0.51%, about 0.52%, or about 0.53%.

The surfactant solution may comprise the cationic counterion at a concentration of about 175 mmol/L to about 800 mmol/L, such about 200 mmol to about 800 mmol, about 400 mmol to about 800 mmol, about 600 mmol to about 800 mmol, about 300 mmol to about 500 mmol, about 400 mmol to about 600 mmol, about 500 mmol to about 700 mmol, about 600 mmol to about 800 mmol, about 700 mmol to about 800 mmol, about 180 mmol/L, about 190 mmol/L, about 200 mmol/L, about 225 mmol/L, about 250 mmol/L, about 275 mmol/L, about 300 mmol/L, about 325 mmol/L, about 350 mmol/L, about 375 mmol/L, about 400 mmol/L, about 450 mmol/L, about 500 mmol/L, about 550 mmol/L, about 600 mmol/L, about 650 mmol/L, about 700 mmol/L, or about 750 mmol/L.

The surfactant solution may comprise lithium ion at a concentration of about 175 mmol/L to about 800 mmol/L, such about 200 mmol to about 800 mmol, about 400 mmol to about 800 mmol, about 600 mmol to about 800 mmol, about 300 mmol to about 500 mmol, about 400 mmol to about 600 mmol, about 500 mmol to about 700 mmol, about 600 mmol to about 800 mmol, about 700 mmol to about 800 mmol, about 180 mmol/L, about 190 mmol/L, about 200 mmol/L, about 225 mmol/L, about 250 mmol/L, about 275 mmol/L, about 300 mmol/L, about 325 mmol/L, about 350 mmol/L, about 375 mmol/L, about 400 mmol/L, about 450 mmol/L, about 500 mmol/L, about 550 mmol/L, about 600 mmol/L, about 650 mmol/L, about 700 mmol/L, or about 750 mmol/L.

The surfactant solution may comprise the cationic counterion at a concentration of about 0.001% (weight/volume) to about 5% such as about 0.01% to about 1.0%, about 0.01% to about 0.10%, about 0.05% to about 0.50%, about 0.10% to about 1.0%, or about 0.5% to about 5.0%.

The surfactant solution may comprise lithium ion at a concentration of about 0.001% (weight/volume) to about 1% such as about 0.01% to about 0.8%, about 0.05% to about 0.60%, about 0.10% to about 0.55%, about 0.20% to about 0.55%, about 0.50% to about 0.55%, about 0.01%, about 0.05%, about 0.10%, about 0.11%, about 0.12%, about 0.13%, about 0.14%, about 0.15%, about 0.16%, about 0.17%, about 0.18%, about 0.19%, about 0.20%, about 0.21%, about 0.22%, about 0.23%, about 0.24%, about 0.25%, about 0.26%, about 0.27%, about 0.28%, about 0.29%, about 0.30%, about 0.31%, about 0.32%, about 0.33%, about 0.34%, about 0.35%, about 0.36%, about 0.37%, about 0.38%, about 0.39%, about 0.40%, about 0.41%, about 0.42%, about 0.43%, about 0.44%, about 0.45%, about 0.46%, about 0.47%, about 0.48%, about 0.49%, about 0.50%, about 0.51%, about 0.52%, about 0.53% or about 0.54%.

The surfactant solution may comprise a cationic counterion at a molar ratio relative to the anionic surfactant of about 1:4 to about 4:1 such as about 1:3 to about 3:1, about 1:2 to about 2:1, about 2:3 to about 3:2, about 3:4 to about 4:3, about 4:5 to about 5:4, about 5:6 to about 6:5, about 6:7 to about 7:6, about 7:8 to about 8:7, about 8:9 to about 9:8, about 9:10 to about 10:9, about 10:11 to about 11:10, or about 1:1.

The surfactant solution may comprise a cationic counterion at a molar ratio relative to the lauryl sulfate of about 1:4 to about 4:1 such as about 1:3 to about 3:1, about 1:2 to about 2:1, about 2:3 to about 3:2, about 3:4 to about 4:3, about 4:5 to about 5:4, about 5:6 to about 6:5, about 6:7 to about 7:6, about 7:8 to about 8:7, about 8:9 to about 9:8, about 9:10 to about 10:9, about 10:11 to about 11:10, or about 1:1.

The surfactant solution may comprise lithium ion at a molar ratio relative to the anionic surfactant of about 1:4 to about 4:1 such as about 1:3 to about 3:1, about 1:2 to about 2:1, about 2:3 to about 3:2, about 3:4 to about 4:3, about 4:5 to about 5:4, about 5:6 to about 6:5, about 6:7 to about 7:6, about 7:8 to about 8:7, about 8:9 to about 9:8, about 9:10 to about 10:9, about 10:11 to about 11:10, or about 1:1.

The surfactant solution may comprise a lithium ion at a molar ratio relative to the lauryl sulfate of about 1:4 to about 4:1 such as about 1:3 to about 3:1, about 1:2 to about 2:1, about 2:3 to about 3:2, about 3:4 to about 4:3, about 4:5 to about 5:4, about 5:6 to about 6:5, about 6:7 to about 7:6, about 7:8 to about 8:7, about 8:9 to about 9:8, about 9:10 to about 10:9, about 10:11 to about 11:10, or about 1:1.

Surfactant solutions comprising 20% lithium lauryl sulfate (weight/volume) allow for convenient measurement, e.g., 4 parts human plasma can be combined with 1 part surfactant solution to result in a treated sample comprising 4% LLS, and 3 parts human plasma can be combined with 1 part surfactant solution to result in a treated sample comprising 5% LLS. Accordingly, in some embodiments, a surfactant solution comprises 20% lithium lauryl sulfate (weight/volume).

In some embodiments, a surfactant solution is essentially free of 4-(2-hydroxyethyl)-1-piperazineethanesulfonic acid (HEPES), succinate, magnetic particles, poly-deoxy-thymidine oligonucleotides, poly-deoxy-thymidine oligonucleotides bound to magnetic particles, 2,2'-dithiodipyridine, ethylenediaminetetraacetate (EDTA), ethylene glycol-bis(β-aminoethyl ether)-N,N,N',N'-tetra acetate (EGTA), ethanol, boric acid, and/or Triton X-100. A surfactant solution may be essentially free of any nucleic acids (e.g., oligonucleotides such as poly-deoxy thymidine). A surfactant solution may be essentially free of any particles (e.g., magnetic particles).

In some embodiments, a surfactant solution lacks 4-(2-hydroxyethyl)-1-piperazineethanesulfonic acid (HEPES), succinate, magnetic particles, poly-deoxy-thymidine oligonucleotides, poly-deoxy-thymidine oligonucleotides bound to magnetic particles, 2,2'-dithiodipyridine, ethylenediaminetetraacetate (EDTA), ethylene glycol-bis(β-aminoethyl ether)-N,N,N',N'-tetra acetate (EGTA), ethanol, boric acid, and/or Triton X-100. A surfactant solution may lack nucleic acids (e.g., oligonucleotides such as poly-deoxy thymidine). A surfactant solution may lack particles (e.g., magnetic particles).

D. Samples

A "sample" as the term is used herein refers to a composition obtained from the blood of an animal (unless this definition conflicts with the explicit context of the term sample). A sample has typically been contacted with at least an anticoagulant (e.g., ethylenediaminetetraacetate, citrate, oxalate), and a sample may have undergone further downstream processing. A sample is optionally unadulterated.

Blood may be obtained from a mammal such as a human of any age, race, ethnicity, or gender. In some embodiments, a sample consists of an aliquot of blood plasma that is characterized in the fact that the blood plasma was obtained from a blood plasma donor.

A sample is typically an aliquot of blood plasma (such as human blood plasma), blood serum (such as human blood serum), or an aliquot of a manufacturing pool of a plasma-derived product (such as a human plasma-derived product). A sample may optionally comprise an aliquot of blood plasma (such as human blood plasma), blood serum (such as human blood serum), or an aliquot of a manufacturing pool of a plasma-derived product (such as a human plasma-derived product), e.g., wherein the aliquot of the blood plasma, blood serum, or manufacturing pool is dispersed within the sample. A manufacturing pool of a plasma-derived product is typically a manufacturing pool including plasma from a single donor rather than a manufacturing pool including pooled plasma from multiple donors because the compositions and methods disclosed herein are typically used to screen plasma from single donors prior to combining the plasma from single donors into pooled plasma from multiple donors. An aliquot of a manufacturing pool may nevertheless include pooled plasma or a downstream manufacturing pool thereof, for example, to allow quality control screening of the pooled plasma or the downstream manufacturing pool thereof.

A sample is typically not whole blood because whole blood contains cells that may interfere with nucleic acid testing and other assays such as ELISA. The sample may nevertheless be or comprise whole blood, for example, for convenience such as to eliminate the centrifugation step that is generally used to obtain blood plasma from whole blood.

A sample optionally comprises an analyte such as a virus of the Parvoviridae family. Many samples will not contain an analyte such as samples obtained from a human subject who has not been exposed to the analyte, for example, wherein the analyte is parvovirus B19.

E. Treated Sample

A "treated sample" as the term is used herein refers to a sample to which an anionic surfactant has been added. A treated sample is generally a liquid composition and the treated sample can optionally include, for example, particulates such as virus particles that are suspended in the liquid composition.

A treated sample typically comprises an anionic surfactant at a concentration of at least about 3% (weight/volume) such as at least about 4% or at least about 5%. In preferred embodiments, a treated sample comprises at least about 4% anionic surfactant such as at least about 4% lauryl sulfate.

A treated sample typically comprises an anionic surfactant at a concentration of about 1% to about 20% (weight/volume) such as about 3% to about 9%, about 4% to about 9%, about 1% to about 5%, about 3% to about 7%, about 5% to about 9%, about 1%, about 2%, about 3%, about 4%, about 5%, about 6%, about 7%, about 8%, about 9%, or about 10%.

A treated sample typically comprises an anionic surfactant at a concentration of at least about 110 mmol/L such as at least about 120 mmol/L, about 130 mmol/L, about 140 mmol/L, about 150 mmol/L, about 160 mmol/L, about 170 mmol/L, about 180 mmol/L, or about 190 mmol/L. In preferred embodiments, a treated sample comprises at least about 150 mmol/L anionic surfactant such as at least about 150 mmol/L lauryl sulfate.

A treated sample typically comprises an anionic surfactant at a concentration of about 100 mmol/L to about 1 mol/L such as about 150 mmol/L to about 500 mmol/L, about 150 mmol/L to about 350 mmol/L, about 100 mmol/L to about 200 mmol/L, about 150 mmol/L to about 250 mmol/L, about 200 mmol/L to about 300 mmol/L, about 250 mmol/L to about 350 mmol/L, about 120 mmol/L, about 130 mmol/L, about 140 mmol/L, about 150 mmol/L, about 160 mmol/L, about 170 mmol/L, about 180 mmol/L, about 190 mmol/L, about 200 mmol/L, about 210 mmol/L, about 220 mmol/L, about 230 mmol/L, about 240 mmol/L, about 250 mmol/L, about 260 mmol/L, about 270 mmol/L, about 280 mmol/L, about 290 mmol/L, or about 300 mmol/L. In preferred embodiments, a treated sample comprises at least 150 mmol/L anionic surfactant such as at least 160 mmol/L, 170 mmol/L, or 180 mmol/L lauryl sulfate.

A treated sample typically comprises less than 300 mmol/L sodium ion such as less than 250 mmol/L, 200 mmol/L, 180 mmol/L, 160 mmol/L, or 150 mmol/L. Human blood serum, for example, typically contains about 135 to 145 mmol/L sodium ion, and thus, a treated sample will typically contain about 100 mmol/L to 145 mmol/L sodium ion depending on its dilution factor.

A treated sample typically comprises less than 0.65% sodium ion (weight/volume) such as less than 0.60%, 0.55%, 0.50%, 0.45%, 0.40%, or 0.35% sodium ion.

A treated sample optionally comprises lithium ion at a concentration of at least about 110 mmol/L such as at least about 120 mmol/L, about 130 mmol/L, about 140 mmol/L, about 150 mmol/L, about 160 mmol/L, about 170 mmol/L, about 180 mmol/L, or about 190 mmol/L. A treated sample optionally comprises at least about 150 mmol/L lithium ion such as at least about 150 mmol/L lithium ion.

A treated sample optionally comprises lithium ion at a concentration of about 100 mmol/L to about 1 mol/L such as about 150 mmol/L to about 500 mmol/L, about 150 mmol/L to about 350 mmol/L, about 100 mmol/L to about 200 mmol/L, about 150 mmol/L to about 250 mmol/L, about 200 mmol/L to about 300 mmol/L, about 250 mmol/L to about 350 mmol/L, about 120 mmol/L, about 130 mmol/L, about 140 mmol/L, about 150 mmol/L, about 160 mmol/L, about 170 mmol/L, about 180 mmol/L, about 190 mmol/L, about 200 mmol/L, about 210 mmol/L, about 220 mmol/L, about 230 mmol/L, about 240 mmol/L, about 250 mmol/L, about 260 mmol/L, about 270 mmol/L, about 280 mmol/L, about 290 mmol/L, or about 300 mmol/L. A treated sample optionally comprises at least 150 mmol/L lithium ion such as at least 160 mmol/L, 170 mmol/L, or 180 mmol/L lithium ion.

The treated sample may comprise lithium ion at a concentration of at least about 0.001% (weight/volume) such as at least about 0.01%, about 0.02%, about 0.03%, about 0.04%, about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, about 0.19%, about 0.20%, about 0.21%, about 0.22%, about 0.23%, about 0.24%, or about 0.25%.

The treated sample may comprise the cationic counterion at a concentration of about 0.001% to about 5% such as about 0.005% to about 2%, or about 0.01% to about 1%.

The treated sample may comprise lithium ion at a concentration of about 0.001% (weight/volume) to about 1% such as about 0.01% to about 0.80%, about 0.05% to about 0.50%, about 0.07% to about 0.40%, about 0.01% to about 0.30%, about 0.10% to about 0.25%, about 0.01%, about 0.02%, about 0.03%, about 0.04%, about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, about 0.19%, about 0.20%, about 0.21%, about 0.22%, about 0.23%, about 0.24%, about 0.25%, about 0.26%, or about 0.27%.

In some embodiments, a treated sample is essentially free of 4-(2-hydroxyethyl)-1-piperazineethanesulfonic acid (HEPES), succinate, magnetic particles, poly-deoxy-thymidine oligonucleotides, poly-deoxy-thymidine oligonucleotides bound to magnetic particles, 2,2'-dithiodipyridine, ethylenediaminetetraacetate (EDTA), ethylene glycol-bis(β-aminoethyl ether)-N,N,N',N'-tetra acetate (EGTA), ethanol, boric acid, and/or Triton X-100.

In some embodiments, a treated sample lacks 4-(2-hydroxyethyl)-1-piperazineethanesulfonic acid (HEPES), succinate, magnetic particles, poly-deoxy-thymidine oligonucleotides, poly-deoxy-thymidine oligonucleotides bound to magnetic particles, 2,2'-dithiodipyridine, ethylenediaminetetraacetate (EDTA), ethylene glycol-bis(β-aminoethyl ether)-N,N,N',N'-tetra acetate (EGTA), ethanol, boric acid, and/or Triton X-100.

F. Analyte

Various aspects of the invention relate to an analyte that is optionally present in a sample or treated sample. An analyte can be, for example, a virus of the Parvoviridae family such as parvovirus B19. An analyte can be, for example, an antigen of a virus of the Parvoviridae family. An analyte can be, for example, an antibody that specifically binds an antigen of a virus of the Parvoviridae family. An analyte can be, for example, a nucleic acid of a virus of the Parvoviridae family. Accordingly, an analyte may optionally be a protein or nucleic acid, and the precise nature of the analyte is not particularly limiting.

G. Assay Compositions

Various aspects of the invention relate to assays to detect an analyte and/or to measure the concentration of an analyte such as a relative concentration (e.g., wherein the concentration is relative to a threshold value) or an absolute concentration. An assay may be, for example, nucleic acid testing such as transcription mediated amplification (TMA) or polymerase chain reaction (PCR).

1. TMA

In some embodiments, the invention relates to a composition comprising a liquid wherein the liquid comprises an anionic surfactant, which is used to treat sample as described herein.

The invention related to a composition also comprising a liquid wherein the liquid comprises at least two amplification primers that each specifically bind either a nucleotide sequence of an analyte or a reverse complement thereof thereby allowing the TMA amplification of the analyte. Among amplification primers, at least one primer, so called promoter primer, comprises a T7 promoter sequence at the 5' end of the primer.

The invention related to a composition also comprising a liquid wherein the liquid comprises at least two enzymes, reverse transcriptase and T7 RNA polymerase, allowing the TMA amplification of the analyte. TMA amplification employs an RNA polymerase, a DNA polymerase, deoxyribonucleoside triphosphates, ribonucleoside triphosphates, and a promoter-template complementary oligonucleotide. In the first step of the amplification, a promoter-primer hybridizes to the target nucleic acid at a defined site. Reverse transcriptase creates a complementary DNA copy of the target nucleic acid by extension from the 3' end of the promoter-primer. Following interaction of an opposite strand primer with the newly synthesized DNA strand, a second strand of DNA is synthesized from the end of the primer by reverse transcriptase, thereby creating a double-stranded DNA molecule. RNA polymerase recognizes the promoter sequence in this double-stranded DNA template and initiates transcription. Each of the newly synthesized RNA amplicons re-enters the TMA process and serves as a template for a new round of replication, thereby leading to an exponential expansion of the RNA amplicon. Since each of the DNA templates can make 100-1000 copies of RNA amplicon, this expansion can result in the production of 10 billion amplicons in less than one hour (see, e.g. U.S. Pat. No. 9,752,201, hereby incorporated by reference in its entirety)

2. PCR

In some embodiments, the invention relates to a composition comprising a liquid wherein the liquid comprises an anionic surfactant, which is used to treat sample as described herein. The invention related to a composition also comprising a liquid wherein the liquid comprises at least two PCR primers that each specifically bind either a nucleotide sequence of an analyte or a reverse complement thereof thereby allowing the PCR amplification of a PCR product of the analyte.

The term "PCR primer" as used herein refers to a single-stranded DNA molecule consisting of 8 to 40 nucleotides that has a melting temperature of at least 50° C. when annealed to its reverse complement.

A composition comprising at least two PCR primers typically comprises each PCR primer of the at least two PCR primers at a concentration of at least 10 nM such as at least 50 nM, at least 100 nM, or at least 200 nM.

A composition comprising at least two PCR primers optionally comprises at least 5 µM dNTPs (i.e., at least 5 µM of each of dATP, dTTP, dCTP, and dGTP) such as at least 10 µM dNTPs, at least 25 µM dNTPs, or at least 50 µM dNTPs.

A composition comprising at least two PCR primers optionally comprises a thermostable DNA polymerase such as Taq polymerase. A thermostable DNA polymerase has a half-life of at least 60 minutes in aqueous solution at 50° C. Human DNA polymerases are not thermostable by definition.

3. Immunoassays

A composition may comprise an antibody or an antigen binding portion thereof. An antibody is typically of a species other than human such as mouse, rat, guinea pig, hamster, rabbit, goat, sheep, pig, cat, monkey, dog, donkey, horse, cow, or chicken.

An antibody may specifically bind an epitope of an analyte. For example, an antibody may specifically bind an epitope of a virus of the Parvoviridae family such as an epitope of parvovirus B19.

An antibody or an antigen binding portion thereof can optionally be covalently or non-covalently tethered to a solid support such as a bead, a membrane, a microtiter plate, a polypeptide chip, or the solid-phase of a chromatography column. An antibody or an antigen binding portion thereof can optionally be covalently or non-covalently bound to a detection label such as a fluorophore, dye, enzyme (e.g., horseradish peroxidase), or radiolabel.

A composition can optionally comprise a primary antibody and a secondary antibody (or an antigen binding portion), wherein the primary antibody and the secondary antibody are antibodies as described herein, the primary antibody specifically binds an analyte, and the secondary antibody specifically binds to the Fc region of the primary antibody.

A composition may comprise a recombinant protein comprising an epitope of an analyte such as a virus of the Parvoviridae family (e.g., an epitope of parvovirus B19). The recombinant protein can be immobilized on a solid support (e.g., a bead, a membrane, a microtiter plate, a polypeptide chip, or the solid-phase of a chromatography column) or covalently or non-covalently bound to a detection label (e.g., a fluorophore, dye, enzyme, or radiolabel).

H. Methods of Measuring a Concentration or Determining a Relative Concentration

Various aspects of the invention relate to a method of determining the concentration of an analyte in a sample. The analyte may be a virus or a nucleic acid of a virus. The analyte may be a virus of the Parvoviridae family or a nucleic acid of a virus of the Parvoviridae family. The analyte may be human parvovirus B19 or a nucleic acid of human parvovirus B19. The sample may be or comprise an aliquot of either blood plasma such as human blood plasma, blood serum such as human blood serum, or a manufacturing pool of a plasma-derived product.

A method may include contacting a sample with a surfactant solution as described herein thereby producing a treated sample. The sample may comprise, for example, an aliquot of blood plasma, blood serum, or a manufacturing pool of a plasma-derived product. The aliquot of blood plasma, blood serum, or a manufacturing pool can optionally be dispersed within the sample or the sample may consist essentially of the aliquot.

Contacting may occur at a temperature below 60° C. such as below about 55° C., about 50° C., about 45° C., about 40° C., or about 37° C. Contacting may occur at a temperature of about 4° C. to about 55° C. such as about 4° C. to about 50° C., about 4° C. to about 40° C., about 20° C. to about 50° C., about 20° C. to about 40° C., about 4° C. to about 37° C., about 4° C. to about 25° C., about 4° C. to about 23° C., about 20° C. to about 37° C., or about 20° C. to about 25° C.

A method may include determining whether the concentration of the analyte is above or below a threshold value. Determining whether the concentration of the analyte is above or below a threshold value may comprise nucleic acid testing such as TMA. For example, the analyte may be human parvovirus B19 or a nucleic acid of human parvovirus B19, and nucleic acid testing may be capable of detecting all known genotypes of human parvovirus B19.

A method may include determining whether the analyte is present and/or detectable in the sample.

A method may include measuring the concentration of the analyte, e.g., thereby obtaining a measurement. Measuring the concentration of an analyte may comprise nucleic acid testing such as TMA. For example, the analyte may be human parvovirus B19 or a nucleic acid of human parvovirus B19, and nucleic acid testing may be capable of detecting all known genotypes of human parvovirus B19.

In some embodiments, the method comprises measuring the concentration of human parvovirus B19 in the sample thereby obtaining a measurement.

In some embodiments, the coefficient of variation of different measurements obtained for different aliquots of the same sample is no more than 50% for aliquots that are contacted with the surfactant solution and that undergo the same sample preparation and analysis steps to determine whether the concentration of analyte in the different aliquots is above or below the threshold value, and the coefficient of variation of different measurements obtained for different aliquots of the same sample is greater than 50% for aliquots that are not contacted with the surfactant solution but that otherwise undergo the same sample preparation and analysis steps to determine whether the concentration of analyte in the different aliquots is above or below the threshold value.

A method may optionally comprise discarding the blood plasma, blood serum, manufacturing pool, or a downstream manufacturing pool of any one of the foregoing if the concentration of the analyte in the aliquot is greater than a threshold value. For example, the analyte may be human parvovirus B19 or a nucleic acid of human parvovirus B19, and the threshold value may be less than or equal to 10,000 IU/mL. For example, the analyte may be human parvovirus B19 or a nucleic acid of human parvovirus B19, and the method may include discarding the blood plasma, blood serum, manufacturing pool, or a downstream manufacturing pool thereof if the concentration of human parvovirus B19 or the concentration of a nucleic acid of human parvovirus B19 is greater than 10,000 IU/mL.

I. Methods of Releasing Blood or a Component Thereof, Preparing Pooled Plasma, or Manufacturing a Plasma-Derived Product Various aspects of the invention relate to a method of determining whether whole blood or a blood component (such as blood serum or blood plasma) can be safely released, e.g., for use in a transfusion. A method may further comprise releasing either whole blood or a blood component associated with a sample for use in a transfusion if the concentration of human parvovirus B19 in an aliquot of the sample is below a threshold value. A method may further comprise withholding either whole blood or a blood component associated with a sample from use in a transfusion if the concentration of human parvovirus B19 in an aliquot of the sample is above a threshold value.

Various aspects of the invention relate to a method of manufacturing a plasma-derived product comprising performing a method of determining the concentration of an analyte in a sample as described herein and manufacturing the plasma-derived product. The plasma-derived product may be, for example, pooled plasma, solvent/detergent treated pooled plasma, a coagulation factor, a fibrin sealant, albumin, or an immunoglobulin product.

Various aspects of the invention relate to a method of preparing pooled plasma comprising performing a method of determining the concentration of an analyte in a sample as described herein, wherein the aliquot is from blood plasma, and the method comprises adding the blood plasma to pooled plasma if the concentration of the analyte is less than a threshold value.

Various aspects of the present invention relate to a plasma-derived product manufactured according to the methods described herein. For example, a plasma-derived product can optionally be manufactured by (1) performing a method of determining the concentration of an analyte in a sample as described herein (e.g., an absolute concentration or a relative concentration), and (2) manufacturing the plasma-derived product if the concentration of the analyte in the sample is allowable, e.g., because the concentration is below a threshold value.

EXEMPLIFICATION

Example 1. State of the Art Analysis of Challenging Plasma Sample GDFL211

Sample GDFL211 was obtained from Biomat USA (Raleigh, N.C.). Sample GDFL211 is a plasma sample containing >10 million IU/mL parvovirus B19. Sample GDFL211 displays no visible clumping, and yet analysis of the sample results in highly variable measurements of parvovirus B19 titer.

10 aliquots of the diluted GDFL211 sample were analyzed using the Procleix Parvo/HAV assay to determine parvovirus B19 titer. Measurements ranged from 1,922 to >100,000 with a coefficient of variation (CV) of 107% (Table 1, Procleix Parvo/HAV). 8 aliquots of the diluted GDFL211 sample were sent to ARUP Laboratories (Salt Lake City, Utah) for testing with a validated quantitative PCR assay that is approved by the New York State Department of Health. Measurements ranged from 884 to 91,700 with a CV of 115% (Table 1, qPCR).

TABLE 1

Analysis of Sample GDFL211 with Standard Protocols to Measure Parvovirus B19 Titer
Parvovirus B19 IU/mL

| Replicate # | Procleix Parvo/HAV | qPCR |
| --- | --- | --- |
| 1 | 22,589 | 20,500 |
| 2 | >100,000 | 33,700 |

TABLE 1-continued

Analysis of Sample GDFL211 with Standard Protocols to Measure Parvovirus B19 Titer
Parvovirus B19 IU/mL

| Replicate # | Procleix Parvo/HAV | qPCR |
| --- | --- | --- |
| 3 | 7,744 | 91,700 |
| 4 | 1,922 | 2,980 |
| 5 | >100,000 | 8,090 |
| 6 | >100,000 | 884 |
| 7 | 15,508 | 44,900 |
| 8 | 8,006 | 9,330 |
| 9 | 71,582 | Not Tested |
| 10 | 20,145 | Not Tested |
| Mean IU/mL | 55,266 | 26,511 |
| % CV | 107 | 115 |
| Max | >100,000 | 91,700 |
| Min | 1,922 | 884 |

Example 2. Screens of Routine Modifications to Sample Preparation Protocols do not Improve Coefficient of Variation for Parvovirus B19 Nucleic Acid Testing Aliquots of diluted sample GDFL211, which were never frozen, were incubated at room temperature on a rocker for 1 hour. Aliquots of diluted sample GDFL211 were frozen, thawed at 4° C. for 24 hours, and then vortexed for 5 seconds. Aliquots of diluted sample GDFL211 were frozen and then thawed on a rocker for 1 hour. Aliquots of diluted sample GDFL211 were frozen, thawed at 30° C. for 30 minutes, and then vortexed for 5 seconds. Aliquots of diluted sample GDFL211 were frozen, thawed at 30° C. for 60 minutes, and then vortexed for 15 minutes. Aliquots of diluted sample GDFL211 were frozen and then rapidly thawed at 37° C. Aliquots of diluted sample GDFL211 were frozen, thawed at 37° C. for 70 minutes, and then mixed by inverting for 5 seconds. Aliquots of diluted sample GDFL211 were frozen and then thawed at 60° C. in a reagent preparation incubator for 45 minutes with rotation. Each sample was then analyzed by nucleic acid testing. Control plasma samples comprising parvovirus B19 that do not display high variability in titer measurements were processed and analyzed in parallel. The foregoing sample preparation strategies resulted in CV's ranging from 58% to 141% for diluted sample GDFL211 and 15% to 24% for the control sample (FIG. 1). Based on these results, freeze-thaw was determined to be unhelpful at improving the coefficient of variation of parvovirus B19 titer measurement in challenging samples.

Figure 2:
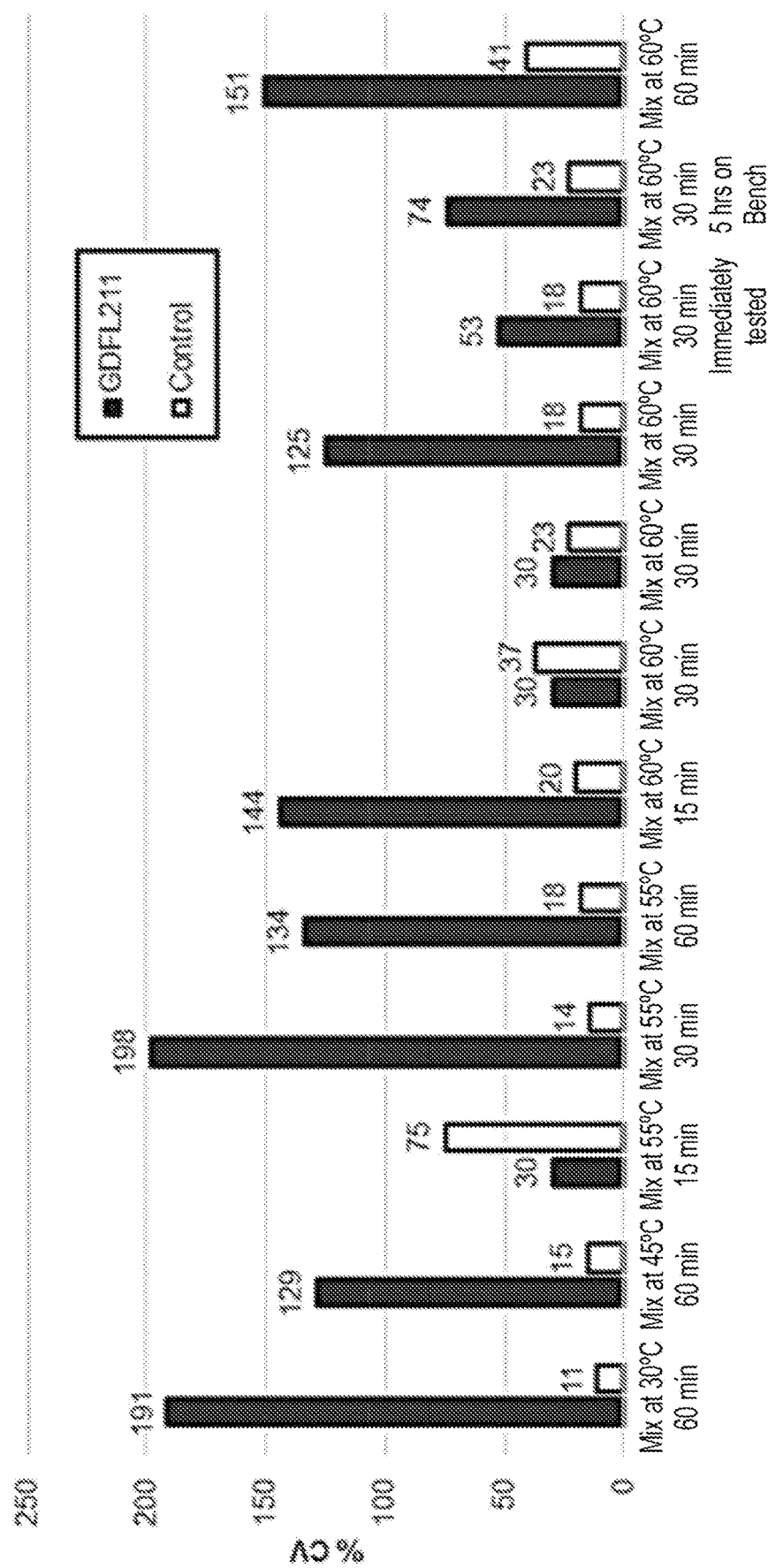
FIG. 2 is a bar graph displaying an analysis of the coefficient of variation (% CV) for aliquots from the challenging plasma sample GDFL211 (black bars) and a control plasma sample (white bars) that were analyzed by nucleic acid testing for parvovirus B19 after heating under a variety of different conditions. Mixing at elevated temperature (60° C.) for 30 minutes appeared to reduce % CV to control levels, but this result was not reproducible. Other mixing/heating conditions did not improve the coefficient of variation among different aliquots of plasma sample GDFL211 that underwent the same heating protocol.

Aliquots of diluted sample GDFL211 were mixed at temperatures ranging from 30° C. to 60° C. for durations of 15 minutes to 60 minutes and then analyzed by nucleic acid testing. Control plasma samples were processed and analyzed in parallel. Mixing at 60° C. for 30 minutes resulted in CV's of 30%, which were comparable to control samples, but this result was not reproducible (FIG. 2). To determine whether the time between incubation at 60° C. and sample analysis affected measurement variance, aliquots of samples that were incubated at 60° C. for 30 minutes were either immediately tested after incubation or allowed to sit for five hours at room temperature prior to testing. Such modifications to the sample preparation protocol did not reproduce the CV of 30%, and thus, the observed CV of 30% obtained after mixing at 60° C. for 30 minutes was found to be a statistical anomaly rather than a real coefficient of variation. Based on these results, incubation at elevated temperature was determined to be unhelpful at improving the coefficient of variation of parvovirus B19 titer measurement in challenging samples.

Figure 3:
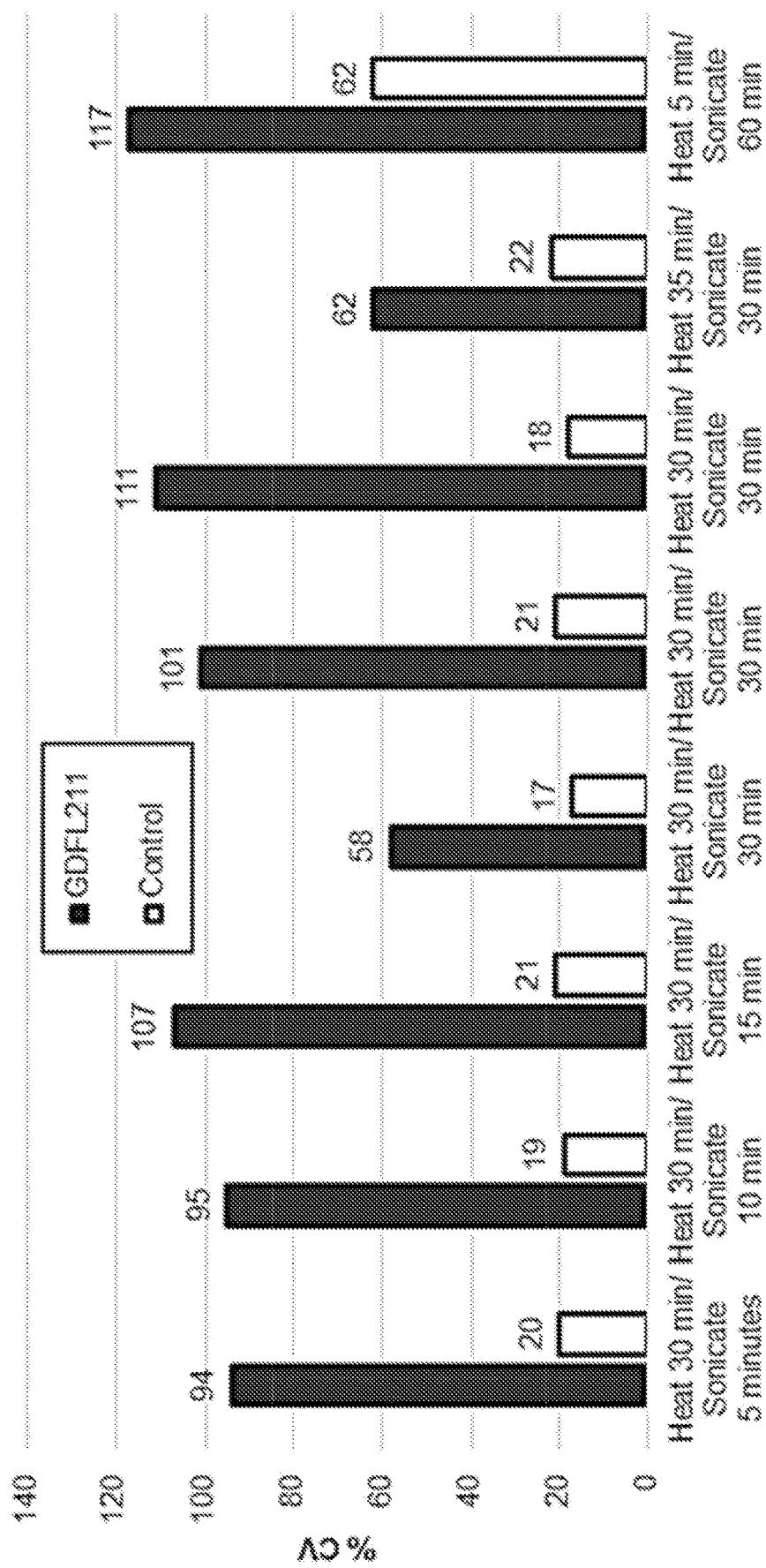
FIG. 3 is a bar graph displaying an analysis of the coefficient of variation (% CV) for aliquots from the challenging plasma sample GDFL211 (black bars) and a control plasma sample (white bars) that were analyzed by nucleic acid testing for parvovirus B19 after heating and sonication under a variety of different conditions. The heating and sonication conditions that were analyzed did not improve the coefficient of variation among different aliquots of plasma sample GDFL211 that underwent the same heating and sonication protocol.

Aliquots of diluted sample GDFL211 were heated for 5 to 30 minutes and then sonicated for 5 to 60 minutes and then analyzed by nucleic acid testing. Control plasma samples were processed and analyzed in parallel. The foregoing sample preparation strategies resulted in CV's ranging from 58% to 117% for sample GDFL211 and 17% to 62% for the control sample (FIG. 3). Based on these results, sonication was determined to be unhelpful at improving the coefficient of variation of parvovirus B19 titer measurement in challenging samples.

Figure 4:
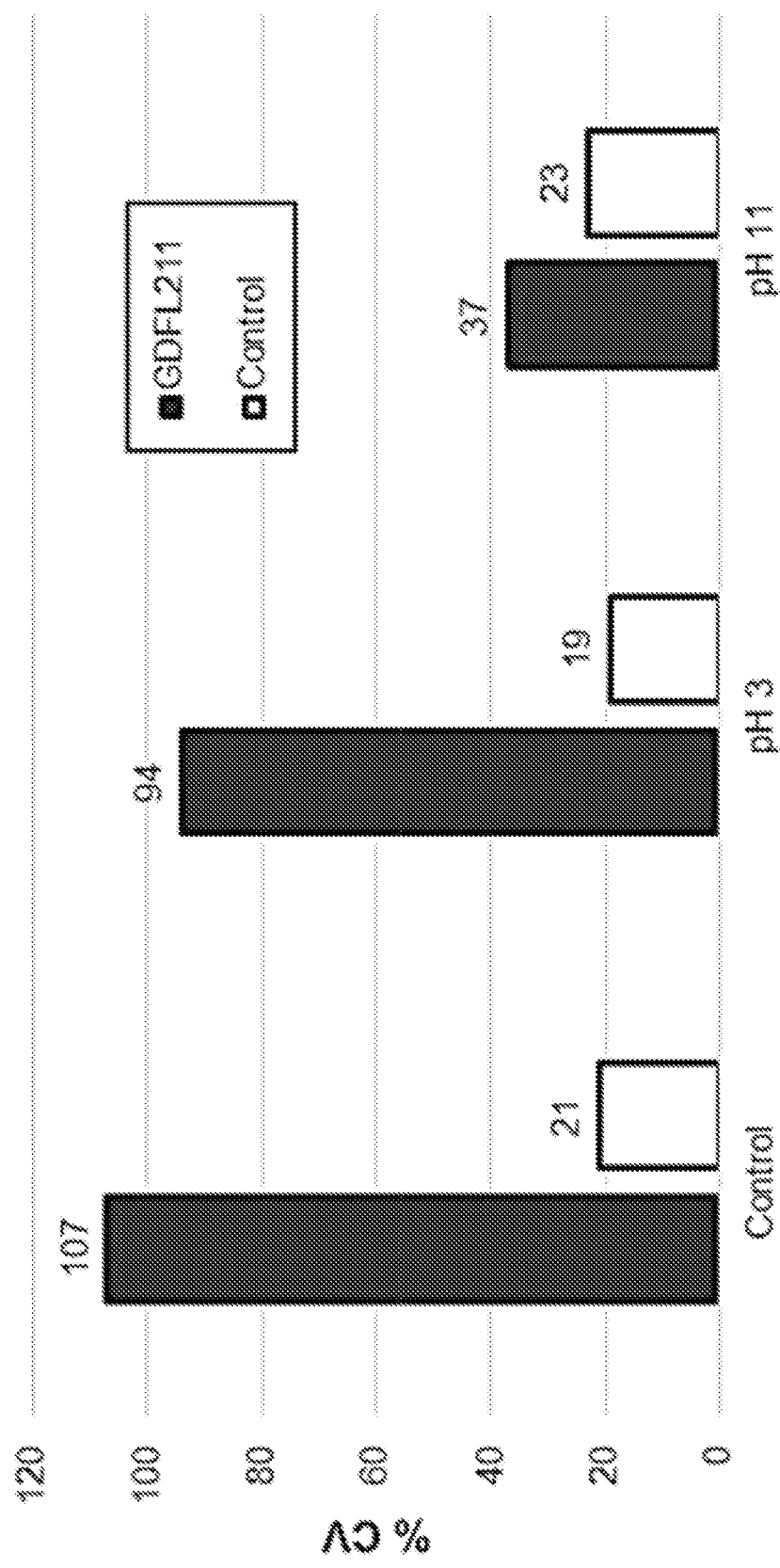
FIG. 4 is a bar graph displaying an analysis of the coefficient of variation (% CV) for aliquots from the challenging plasma sample GDFL211 (black bars) and a control plasma sample (white bars) that were analyzed by nucleic acid testing for parvovirus B19 at neutral pH, pH=3, and pH=11. Analysis at pH=11 appeared to improve the coefficient of variation among different aliquots of plasma sample GDFL211, but these conditions were rejected as undesirable because alkaline pH substantially reduces RNA half-life.

The pH of aliquots of diluted sample GDFL211 was adjusted to pH 3, pH 11, or not adjusted. The pH of aliquots of a control plasma sample was adjusted in parallel. Each sample was then analyzed by nucleic acid testing. The pH of 11 was found to allow for favorable CV's (FIG. 4). High-pH sample analysis is unfavorable, however, because high pH reduces RNA half-life. The pH of 3 resulted in a CV of 94% and neutral pH resulted in a CV of 107% for sample GDFL211. Based on these results, the adjustment of pH was determined to be unhelpful at improving the coefficient of variation of parvovirus B19 titer measurement in challenging samples.

Figure 5:
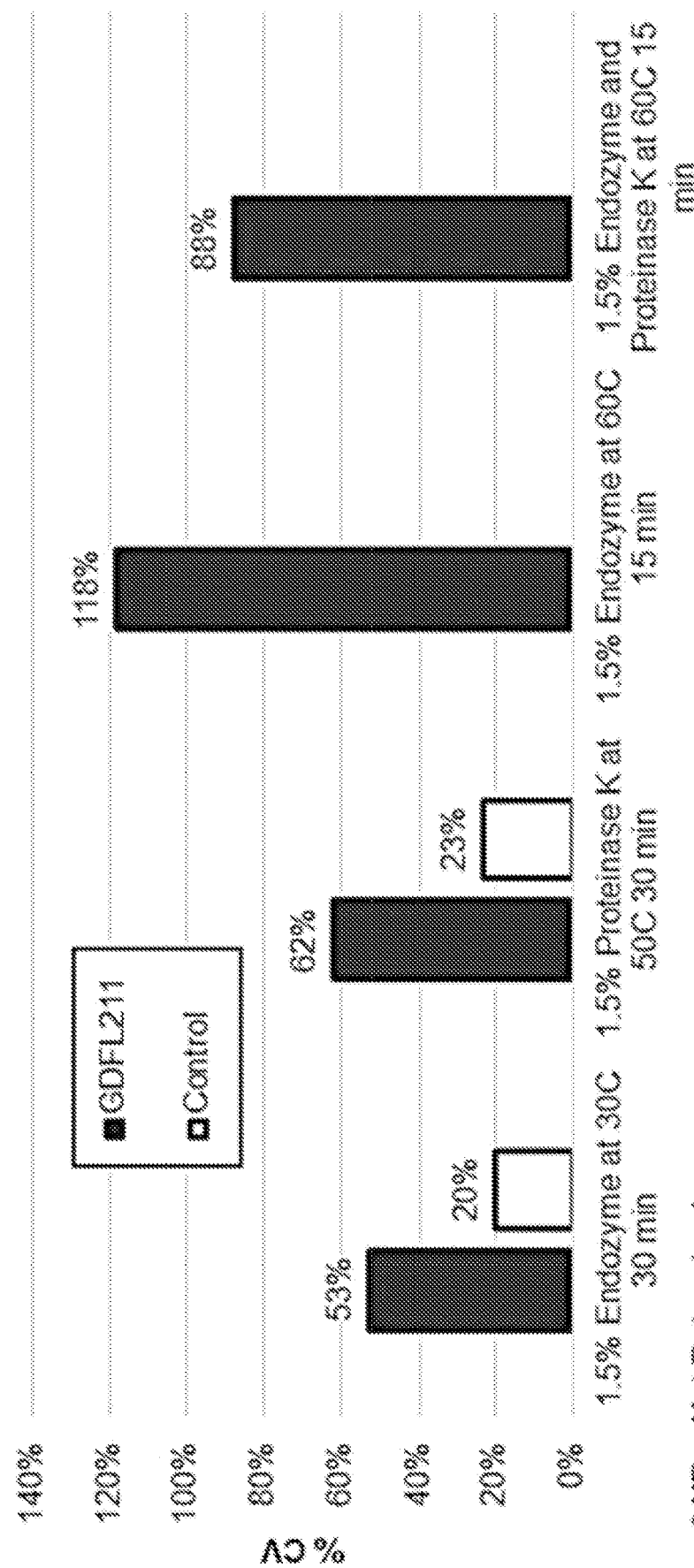
FIG. 5 is a bar graph displaying an analysis of the coefficient of variation (% CV) for aliquots from the challenging plasma sample GDFL211 (black bars) and a control plasma sample (white bars) that were analyzed by nucleic acid testing for parvovirus B19 after different protease treatments. The proteases that were analyzed did not improve the coefficient of variation among different aliquots of plasma sample GDFL211 that underwent the same protease treatments.

Aliquots of sample GDFL211 were incubated with proteases EndoZyme® (Hyglos GmbH, Germany; recombinant Factor C) and/or proteinase K and then analyzed by nucleic acid testing. Control plasma samples were processed and analyzed in parallel. Each enzyme was used at 1.5% concentration. EndoZyme® samples were incubated at 30° C. or 60° C. for 30 minutes. Proteinase K samples were incubated at 50° C. for 30 minutes. The EndoZyme®/proteinase K samples were incubated at 60° C. for 15 minutes. The foregoing sample preparation strategies resulted in CV's ranging from 53% to 118% for sample GDFL211 and 20% to 23% for the control sample (FIG. 5). Based on these results, protease treatment was determined to be unhelpful at improving the coefficient of variation of parvovirus B19 titer measurement in challenging samples.

Example 3. Substitution of Sodium Cation of Sodium Dodecyl Sulfate for Lithium Cation Surprisingly Reduces Coefficient of Variation Commonly-used surfactants sodium dodecyl sulfate (SDS) and Triton X-100 were added to aliquots of sample GDFL211 and then the aliquots were analyzed by nucleic acid testing. SDS displayed low CV's, but samples containing SDS formed precipitates and produced invalid results. Triton X-100 was determined to be unhelpful at improving the coefficient of variation of parvovirus B19 measurements in challenging samples. Surprisingly, however, the mere substitution of the sodium cation of SDS for lithium improved sample CV's and allowed for valid results. In other words, the use of lithium lauryl sulfate (which is also known as both LLS and lithium dodecyl sulfate) instead of SDS (which is also known as both sodium lauryl sulfate and SLS) unexpectedly improved the coefficient of variation of parvovirus B19 measurements in challenging samples. Specifically, the following experiments were performed.

Figure 6:
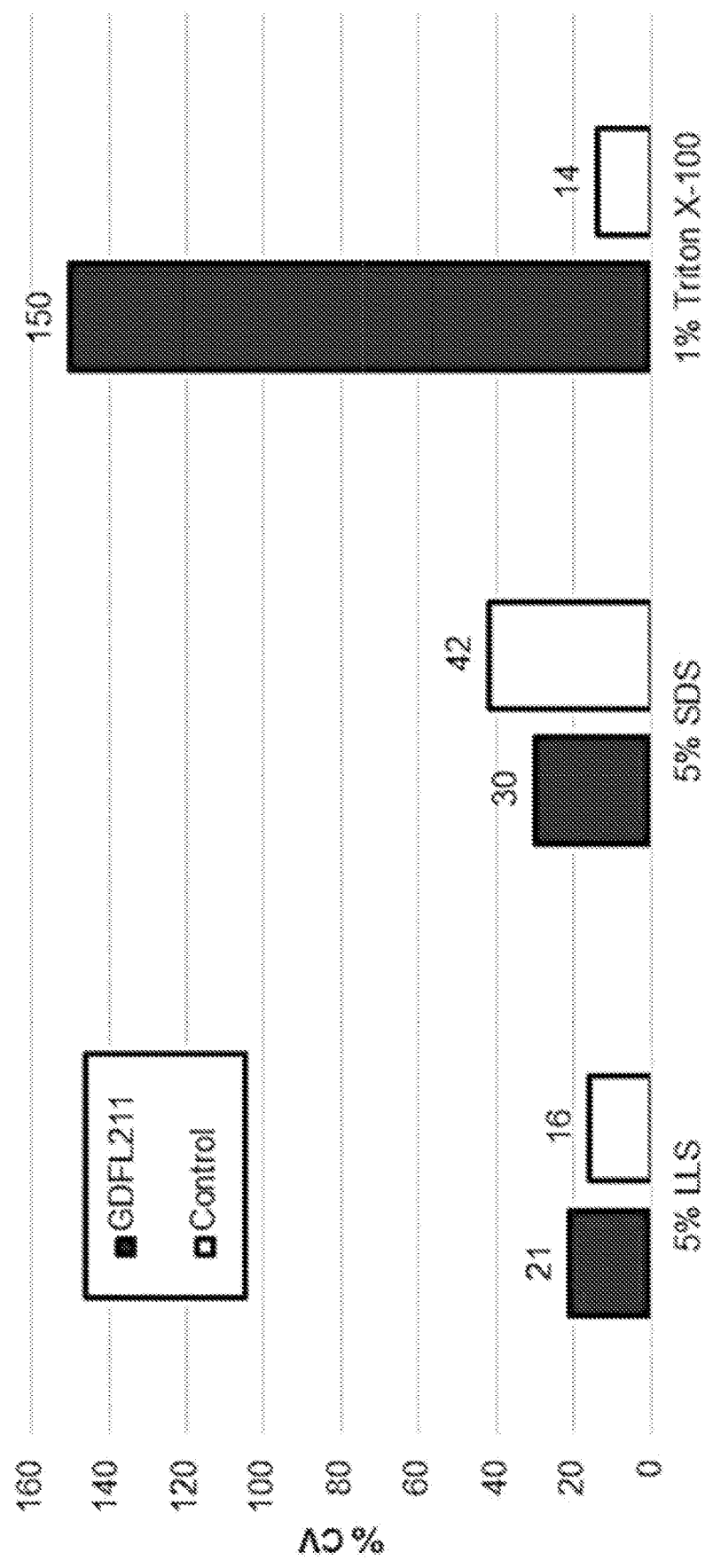
FIG. 6 is a bar graph displaying an analysis of the coefficient of variation (% CV) for aliquots from the challenging plasma sample GDFL211 (black bars) and a control plasma sample (white bars) that were analyzed by nucleic acid testing for parvovirus B19 after the addition of different surfactants. 5% lithium lauryl sulfate (LLS) improved % CV in the analysis of plasma sample GDFL211. The 5% sodium dodecyl sulfate (SDS) samples contained precipitates, which resulted in invalid test results. 1% Triton X-100 did not improve % CV.

Aliquots of diluted sample GDFL211 were contacted with a surfactant solution comprising LLS thereby resulting in treated samples comprising 5% LLS. Aliquots of sample GDFL211 were contacted with a surfactant solution comprising SDS thereby resulting in treated samples comprising 5% SDS. Aliquots of diluted sample GDFL211 were contacted with a surfactant solution comprising the uncharged surfactant Triton X-100 thereby resulting in treated samples comprising 1% Triton X-100. Each sample was then analyzed by nucleic acid testing. Control plasma samples comprising parvovirus B19 that do not display high variability in titer measurements were processed and analyzed in parallel. The treated GDFL211 samples comprising 5% LLS displayed a CV of 21% (FIG. 6). The treated control samples comprising 5% LLS displayed a CV of 16% (FIG. 6). The treated samples comprising 5% SDS similarly displayed low CV's (FIG. 6), but these samples contained precipitates, and results obtained from treated samples comprising 5% SDS were found invalid. The treated GDFL211 samples comprising 1% Triton X-100 displayed a CV of 150% (FIG. 6). Based on these results, SDS and Triton X-100 were determined to be unhelpful at improving the coefficient of variation of parvovirus B19 titer measurements in challenging samples, and LLS was found to improve the coefficient of variation of parvovirus B19 measurements in challenging samples. Notably, both the charge of the surfactant (i.e., anionic surfactant versus uncharged surfactant) and the counter ion of an anionic surfactant (i.e., lithium versus sodium) were found to affect the reduction in coefficient of variation displayed in samples treated with surfactant.

Example 4. Determination of LLS Working Range

Aliquots of diluted sample GDFL211 were contacted with surfactant solutions comprising the anionic surfactant lauryl sulfate and counterion lithium thereby producing treated samples comprising 3% LLS, 4% LLS, 5% LLS, 6% LLS, 7% LLS, 8% LLS, and 9% LLS. The treated samples were analyzed by nucleic acid testing. Control plasma samples were processed and analyzed in parallel. The 3% LLS, 4% LLS, 5% LLS, 6% LLS, 7% LLS, 8% LLS, and 9% LLS-treated GDFL211 samples displayed CV's of 104%, 65%, 20%, 30%, 17%, 18%, and 31%, respectively (FIG. 7). Treated control samples displayed CV's ranging from 19% to 30%. Based on these results, it was determined that LLS concentrations of about 4% and greater are helpful at improving the coefficient of variation of parvovirus B19 titer measurement in challenging samples. Specifically, 4% LLS improved measurement variance relative to 3% LLS, and 5% LLS improved measurement variance relative to 4% LLS (FIG. 7).

Example 5. Analysis of Storage Conditions of LLS-Treated Samples

Aliquots of sample GDFL211 were contacted with surfactant solutions comprising lithium lauryl sulfate, thereby producing treated samples comprising 4% LLS, 5% LLS, 6% LLS, and 7% LLS, and then either refrigerated for 24 hours at 2-8° C. or frozen for 72 hours at −20° C., and then quickly thawed at 37° C.

Figure 7:
FIG. 7 is a bar graph displaying an analysis of the coefficient of variation (% CV) for aliquots from the challenging plasma sample GDFL211 (black bars) and a control plasma sample (white bars) that were analyzed by nucleic acid testing for parvovirus B19 after the addition of lithium lauryl sulfate (LLS) at concentrations of 3% LLS, 4% LLS, 5% LLS, 6% LLS, 7% LLS, 8% LLS, and 9% LLS. The 4% LLS-treated sample displayed an improved % CV relative to the 3% LLS-treated sample, and the 5% LLS-treated sample displayed an improved % CV relative to the 4% LLS-treated sample.
Figure 8:
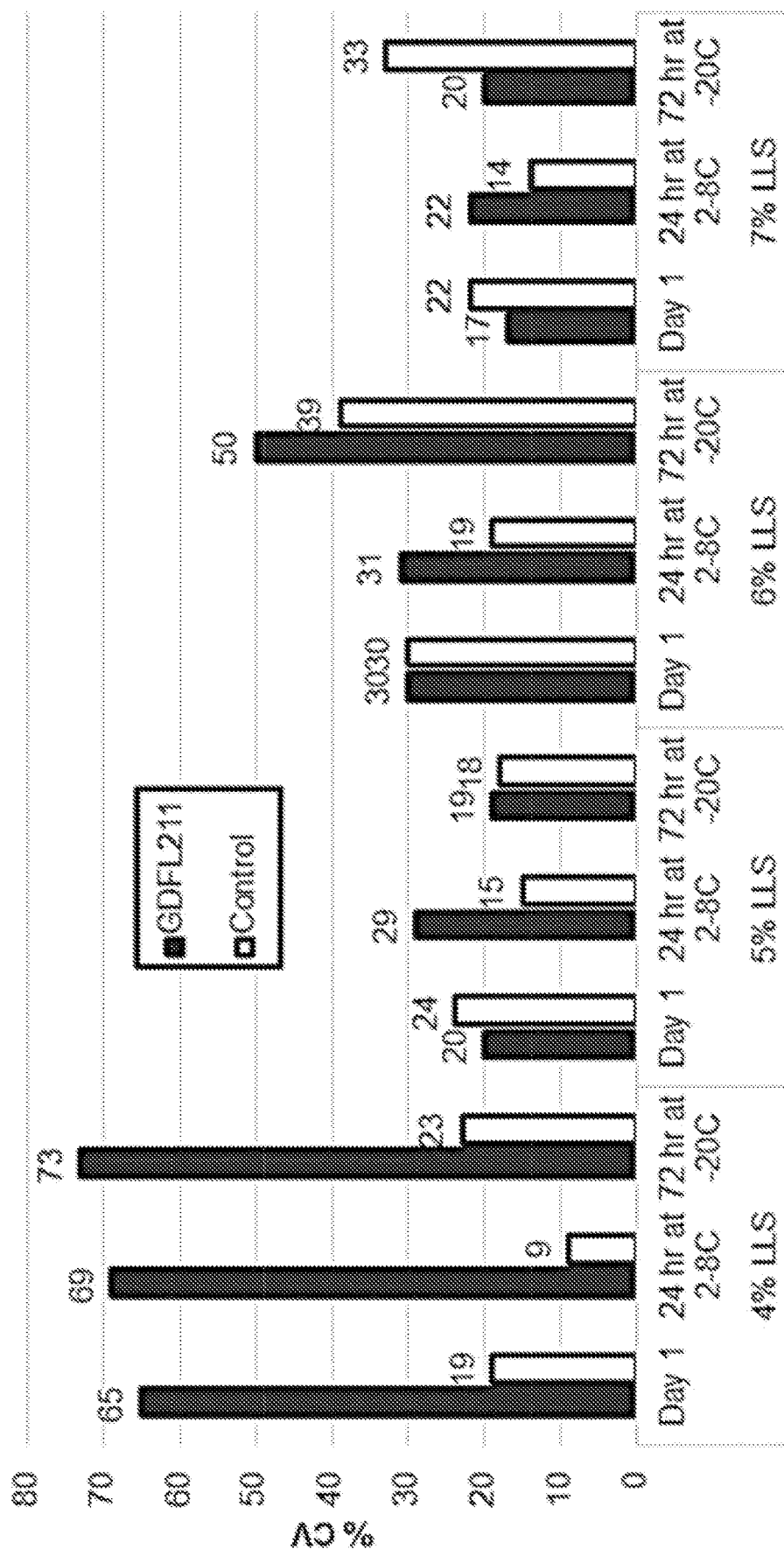
FIG. 8 is a bar graph displaying an analysis of the coefficient of variation (% CV) for aliquots from the challenging plasma sample GDFL211 (black bars) and a control plasma sample (white bars) that were analyzed by nucleic acid testing for parvovirus B19 after the addition of lithium lauryl sulfate (LLS) at concentrations of 4% LLS, 5% LLS, 6% LLS, or 7% LLS and either no storage, refrigeration for 24 hours at 2-8° C., or freezing for 72 hours at ≤−20° C. The 5% LLS-treated samples displayed improved % CV relative to the 4% LLS-treated samples. Refrigeration and freezing were found to have no effect on the LLS-associated improvement of % CV.

The treated samples were analyzed by nucleic acid testing. Control plasma samples were processed and analyzed in parallel. Storage by either refrigeration or freezing was found that have no effect on the coefficient of variation of LLS-treated samples. 4% to 7% LLS was found to improve the coefficient of variation in all GDFL211 samples to which it was added (FIG. 8) relative, for example, to 3% LLS (FIG. 7).

Example 6. Analysis of LLS-Treated Samples for Hepatitis a Virus RNA

Figure 9:
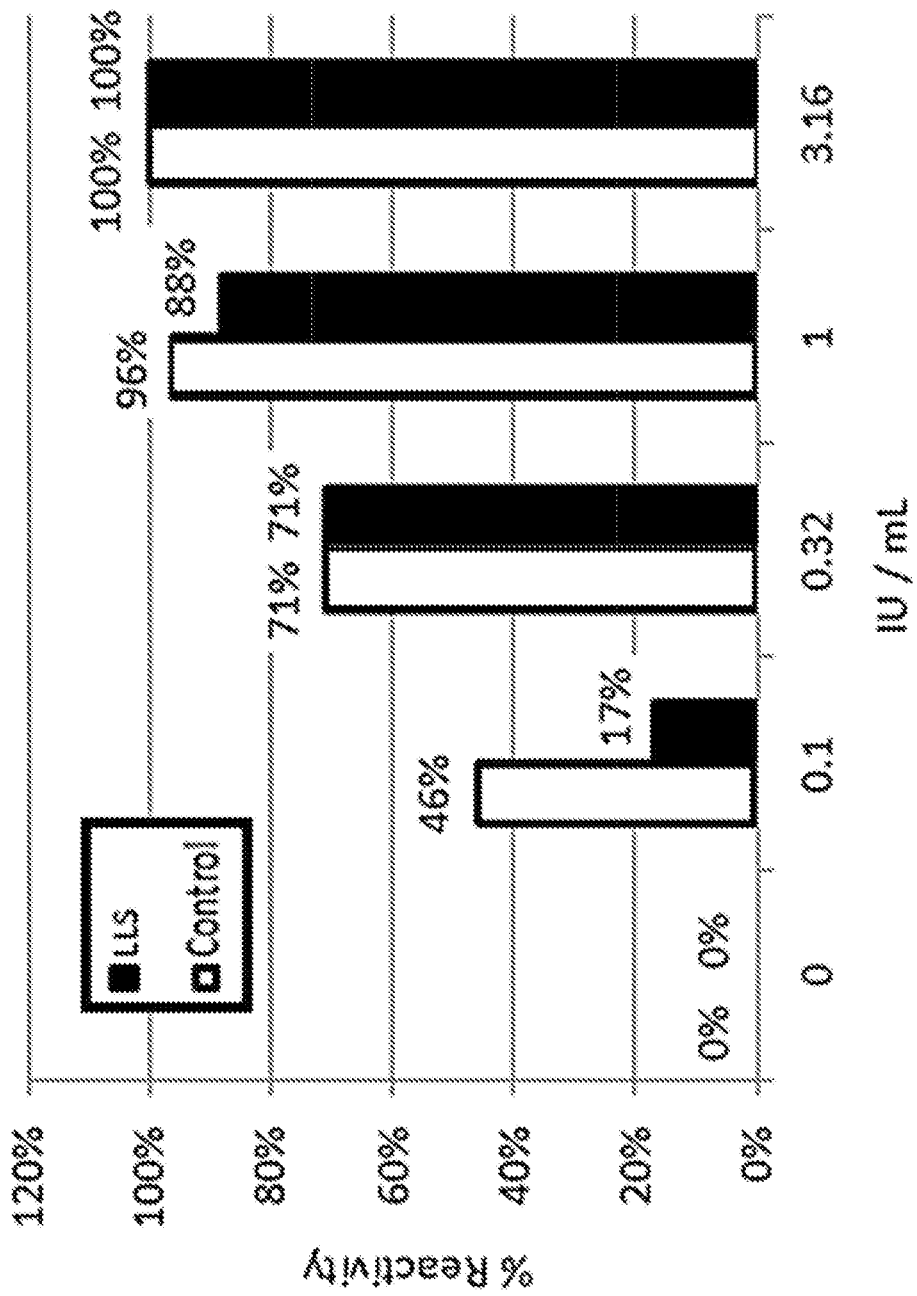
FIG. 9 is a bar graph displaying an analysis of the detection of hepatitis A virus RNA in different dilutions of WHO International Standard for HAV RNA (NIBCS code 00/560) that were either treated with LLS (black bars) or untreated (white bars). The addition of LLS to the HAV RNA standard did not affect the sensitivity of nucleic acid testing of the LLS-treated samples relative to the untreated samples.

Aliquots of the World Health Organization's First International Standard for Hepatitis A Virus RNA (National Institute for Biological Standards and Control code: 00/560) were serially diluted, treated with LLS or untreated (as a control), and then analyzed by nucleic acid testing. The addition of LLS to serially-diluted samples did not affect the sensitivity of Hepatitis A Virus RNA detection based on prohibit and statistical analysis (Table 2 and FIG. 9).

TABLE 2

| Hepatitis A Virus RNA Probit Analysis | | | | |
|---|---|---|---|---|
| Condition | Detection Probability | IU/mL | 95% Fiducial Limits | |
| Untreated | 50% | 0.13 | 0.04 | 0.21 |
|  | 95% | 0.97 | 0.58 | 2.98 |
| LLS-Treated | 50% | 0.25 | 0.14 | 0.37 |
|  | 95% | 1.23 | 0.80 | 2.71 |

Example 7. Analysis of Accuracy of Parvovirus B19 Concentration in LLS-Treated Samples 60 aliquots of a pooled plasma sample containing 10,000 IU/mL parvovirus B19 were mixed with 20% LLS solution to a final LLS concentration of 6% or untreated. LLS-treated samples displayed an average parvovirus B19 concentration of 5370 IU/mL ($10^{3.73}$) whereas untreated samples displayed an average parvovirus B19 concentration of 10,965 IU/mL ($10^{4.04}$).

TABLE 3

| Replicate Measurements of LLS-Treated and Untreated Pooled Plasma Samples | | |
|---|---|---|
| Replicate | Treated | Untreated |
| #1 | 3.66 | 4.07 |
| #2 | 3.63 | 3.98 |
| #3 | 3.86 | 3.99 |
| #4 | 3.76 | 3.96 |
| #5 | 3.82 | 4.04 |
| #6 | 3.71 | 4.04 |
| #7 | 3.78 | 4.11 |
| #8 | 3.93 | 4.04 |
| #9 | 3.72 | 4.12 |
| #10 | 3.45 | 4.07 |
| #11 | 3.61 | 4.04 |
| #12 | 3.63 | 3.96 |
| #13 | 3.91 | 3.98 |
| #14 | 3.85 | 4.12 |
| #15 | 3.72 | 4.09 |
| #16 | 3.68 | 4.02 |
| #17 | 3.65 | 3.88 |
| #18 | 3.93 | 3.88 |
| #19 | 3.77 | 4.22 |
| #20 | 3.49 | 4.14 |
| #21 | 3.63 | 3.91 |
| #22 | 3.57 | 4.03 |
| #23 | 3.86 | 4.05 |
| #24 | 3.82 | 4.04 |
| #25 | 3.74 | 3.97 |
| #26 | 3.75 | 3.93 |
| #27 | 3.69 | 3.98 |
| #28 | 4.00 | 4.25 |
| #29 | 3.70 | 3.99 |
| #30 | 3.49 | 3.96 |

Aliquots of the pooled plasma containing 10,000 IU/mL parvovirus B19 were mixed with 20% LLS solution to a final LLS concentration of 6% or untreated. The aliquots were refrigerated at 2-8° C. for 6 days or frozen at ≤−20° C. for 6 days and then rapidly thawed at 37° C. Average parvovirus quantitation was unaffected by these storage conditions (Table 4).

TABLE 4

| Refrigeration and Freezing Does Not Affect Parvovirus B12 Measurement Accuracy in LLS-Treated Samples | | |
|---|---|---|
| Storage Condition | Untreated Sample | LLS-Treated Sample |
| No Storage | 4.04 | 3.73 |
| Refrigeration at 2-8° C. for 6 days | 4.15 | 3.80 |
| Freezing at ≤ −20° C. for 6 days | 4.05 | 3.77 |

Aliquots of plasma containing parvovirus B19 were diluted at various concentrations and then mixed with 20% LLS solution to a final LLS concentration of 6% or left untreated. LLS did not affect the accuracy or precision of parvovirus B19 measurement at concentrations ranging from 300 IU/mL ($10^{2.48}$ IU/mL) to 30,000 IU/mL ($10^{4.48}$ IU/mL) in these samples (Table 5).

TABLE 5

Parvovirus B19 Concentration Does Not Affect Measurement Accuracy or Precision in LLS-Treated Samples

| Target in Log IU/mL | 4.48 | 4.00 | 3.48 | 3.00 | 2.48 |
|---|---|---|---|---|---|
| Replicate | | | Untreated | | |
| #1 | 4.98 | 4.26 | 3.92 | 3.37 | 2.70 |
| #2 | 4.96 | 4.40 | 3.77 | 3.44 | 2.62 |
| #3 | 4.87 | 4.38 | 3.75 | 3.36 | 2.92 |
| #4 | 4.70 | 4.31 | 3.96 | 3.35 | 2.63 |
| #5 | 4.91 | 4.33 | 3.89 | 3.20 | 2.72 |
| #6 | 4.95 | 4.28 | 3.82 | 3.38 | 2.80 |
| #7 | 4.90 | 4.41 | 3.82 | 3.39 | 2.66 |
| Average Log IU/mL | 4.90 | 4.34 | 3.85 | 3.36 | 2.72 |
| Replicate | | | LLS-Treated | | |
| #1 | 4.66 | 4.14 | 3.57 | 3.16 | 2.56 |
| #2 | 4.58 | 4.04 | 3.40 | 3.10 | 2.47 |
| #3 | 4.65 | 3.99 | 3.52 | 2.95 | 2.48 |
| #4 | 4.80 | 4.14 | 3.56 | 3.12 | 2.50 |
| #5 | 4.79 | 4.14 | 3.59 | 3.06 | 2.48 |
| #6 | 4.57 | 4.20 | 3.57 | 3.15 | 2.63 |
| #7 | 4.58 | 4.07 | 3.52 | 3.09 | 2.30 |
| #8 | 4.55 | 3.97 | 3.47 | 3.08 | 2.33 |
| #9 | 4.68 | 4.16 | 3.73 | 3.13 | 2.71 |
| #10 | 4.69 | 4.12 | 3.63 | 3.12 | 2.47 |
| Average Log IU/mL | 4.65 | 4.10 | 3.56 | 3.10 | 2.49 |

Aliquots of actual plasma samples containing >100,000 IU/mL parvovirus B19 were serially diluted with pooled plasma to fall into the dynamic range of the parvovirus B19 assay and then mixed with 20% LLS solution to a final LLS concentration of 6% or left untreated. LLS treatment generally improved measurement precision as evidence by low coefficients of variation for a group of replicates relative to untreated aliquots (Table 6).

TABLE 6

LLS-Treatment Improves the Precision of Parvovirus B19 Titer Measurement in Samples Containing >100,000 IU/mL Virus Relative to Untreated Samples

| Sample ID | 696332194 | 696338087 | 696340243 | 217503400 | 21751410 |
|---|---|---|---|---|---|
| | | | Untreated | | |
| #1 | 1200 | 38070 | 34867 | 1227 | 12455 |
| #2 | 1251 | 6051 | 20999 | 1377 | 5972 |
| #3 | 1652 | 9355 | 38987 | 31579 | 3082 |
| #4 | 1425 | 19950 | 6015 | 2580 | 3590 |
| #5 | 1228 | 3414 | 16516 | 29080 | 12153 |
| #6 | 1101 | 4847 | 37465 | 6043 | 43009 |
| #7 | 1421 | 47029 | 50641 | 5576 | 15762 |
| % CV | 14 | 96 | 52 | 120 | 101 |
| Avg IU/mL | 1,325 | 18,388 | 29,356 | 11,066 | 13,718 |
| Sample | 696332194 | 696338087 | 696340243 | 217503400 | 21751410 |
| | | | LLS-Treated | | |
| #1 | 965 | 20207 | 15002 | 4337 | 11950 |
| #2 | 773 | 22447 | 15074 | 3489 | 12166 |
| #3 | 953 | 15544 | 9541 | 5788 | 8537 |
| #4 | 1319 | 14672 | 14807 | 5554 | 6745 |
| #5 | 1507 | 11772 | 17378 | 5402 | 9759 |
| #6 | 774 | 20913 | 12119 | 4329 | 10090 |
| #7 | 976 | 21916 | 10048 | 3444 | 7839 |
| % CV | 27 | 23 | 22 | 21 | 21 |
| Avg IU/mL | 1,038 | 18,210 | 13,424 | 4,620 | 9,584 |

The invention claimed is:

1. A method of determining the concentration of human parvovirus B19, comprising:
    contacting a sample with a surfactant solution thereby producing a treated sample, wherein the sample comprises an aliquot of either human blood plasma or a manufacturing pool of a human plasma-derived product and further wherein the surfactant solution comprises an anionic surfactant and a cation and is essentially free of 4-(2-hydroxyethyl)-1-piperazineethanesulfonic acid (HEPES); and
    determining whether the concentration of human parvovirus B19 in the aliquot is above or below a threshold value by assaying the treated sample of human parvovirus B19,
    wherein:
    sodium to the anionic surfactant in the surfactant solution is of a molar ratio of less than 1:10.

2. The method of claim 1, wherein the anionic surfactant is lauryl sulfate.

3. The method of claim 1, wherein the surfactant solution consists of the anionic surfactant, the cation, and water.

4. The method of claim 1, wherein the contacting occurs at a temperature of about 4° C. to about 37° C.

5. The method of claim 1, wherein the cation is a lithium cation and the molar ratio of the lithium cation to the anionic surfactant in the surfactant solution is about 1:2 to about 2:1.

6. The method of claim 1, wherein the concentration of the anionic surfactant in the treated sample is at least 4% by weight/volume.

7. The method of claim 1, wherein assaying the treated sample comprises nucleic acid testing.

8. The method of claim 7, wherein the nucleic acid testing comprises transcription mediated amplification or PCR.

9. The method of claim 7, wherein the nucleic acid testing is capable of detecting all known genotypes of human parvovirus B19.

10. The method of claim 1, further comprising discarding the human blood plasma, the manufacturing pool, or a downstream manufacturing pool thereof if the concentration of human parvovirus B19 in the aliquot is greater than the threshold value.

11. The method of claim 1, further comprising measuring the concentration of human parvovirus B19 in the sample thereby obtaining a measurement, wherein:

the coefficient of variation of different measurements obtained for different aliquots of the same human blood plasma or the same manufacturing pool is no more than 50% for aliquots that are contacted with the surfactant solution and that undergo the same sample preparation and analysis steps to determine whether the concentration of human parvovirus B19 in the different aliquots is above or below the threshold value; and the coefficient of variation of different measurements obtained for different aliquots of the same human blood plasma or the same manufacturing pool is greater than 50% for aliquots that are not contacted with the surfactant solution but that otherwise undergo the same sample preparation and analysis steps to determine whether the concentration of human parvovirus B19 in the different aliquots is above or below the threshold value.

12. A method of manufacturing a plasma-derived product, comprising:

performing the method of claim 1; and manufacturing a plasma-derived product from the human blood plasma or the manufacturing pool if the concentration of human parvovirus B19 in the tested sample is less than the threshold value.

13. The method of claim 12, wherein the plasma-derived product is pooled plasma, solvent/detergent treated pooled plasma, a coagulation factor, a fibrin sealant, albumin, or an immunoglobulin product.

14. A plasma-derived product manufactured according to the method of claim 12.

15. A composition comprising:
a Parvoviridae virus genome;

a surfactant solution consisting an anionic surfactant, a cation and water; and at least two amplification primers that each specifically bind either a nucleotide sequence of a Parvoviridae virus genome or a reverse complement thereof thereby allowing the amplification of a Parvoviridae virus nucleotide sequence, wherein:

the composition comprises a liquid;

the liquid comprises the Parvoviridae virus genome and the surfactant solution; and the molar ratio of the anionic surfactant to any sodium ion present in the liquid is greater than 1:1.

16. The composition of claim 15, wherein the at least two amplification primers allow for the amplification of a nucleotide sequence of each known genotype of human parvovirus B19.

17. The composition of claim 15, further comprising a solid support, wherein:

the solid support is a bead, a membrane, a microtiter plate, a polypeptide chip, or the solid-phase of a chromatography column; and an oligonucleotide is immobilized on the solid support.

18. The composition of claim 15, wherein the anionic surfactant comprises an aliphatic chain comprising 6 to 26 carbon atoms.

19. The composition of claim 18, wherein the aliphatic chain is saturated.

20. The composition of claim 18, wherein the aliphatic chain is unbranched.

21. The composition of claim 18, wherein the anionic surfactant lacks an unbranched, linear carbon chain other than the aliphatic chain.

22. The composition of claim 18, wherein the anionic surfactant lacks any carbon atoms other than the carbon atoms of the aliphatic chain.

23. The composition of claim 15, wherein the anionic surfactant has a net charge of about −1 at pH 5 to 10.

24. The composition of claim 15, wherein the anionic surfactant is an organosulfate, sulfonate, organophosphate, organophosphonate, or carboxylate.

25. The composition of claim 15, wherein the anionic surfactant is lauryl sulfate.

26. The composition of claim 15, wherein the concentration of the anionic surfactant in the liquid is at least 4% (weight/volume).

27. The composition of claim 26, wherein the concentration of the anionic surfactant in the liquid is about 4% to about 9% (weight/volume).

28. The composition of claim 15, wherein the concentration of sodium ion in the liquid is less than 1% (weight/volume).

29. The composition of claim 15, wherein the cation is a lithium cation and further the concentration of the lithium cation in the liquid is at least 0.01% by weight/volume.

30. The composition of claim 15, wherein the Parvoviridae virus genome is of parvovirus B19.

31. The composition of claim 15, wherein the composition comprises human blood plasma or a manufacturing pool of a human plasma-derived product.

32. The composition of claim 15, wherein:

the Parvoviridae virus genome is of parvovirus B19;

the anionic surfactant is lauryl sulfate;

the concentration of lauryl sulfate in the liquid is at least 4% (weight/volume);

the cation is a lithium cation and the concentration of the lithium cation in the liquid is at least 0.1% (weight/volume);

the lithium cation and lauryl sulfate are present in the liquid at a molar ratio of about 11:10 to about 10:11;

the concentration of sodium ion in the liquid is less than 0.5% (weight/volume);

an aliquot of either human blood plasma or a manufacturing pool of a human plasma-derived product is dispersed within the composition; and the Parvoviridae virus genome of the composition is from the aliquot of the human blood plasma or the aliquot of the manufacturing pool.

* * * * *